(12) United States Patent
Angle et al.

(10) Patent No.: US 11,607,386 B2
(45) Date of Patent: Mar. 21, 2023

(54) LIPOSOMES ENCAPSULATING ADENOSINE

(71) Applicant: New York University, New York, NY (US)

(72) Inventors: Siddhesh R. Angle, Jersey City, NJ (US); Carmen Corciulo, Gothenburg (SE); Bruce N. Cronstein, New York, NY (US); Jonathan Kaufman, Pittsburgh, PA (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 17/601,032

(22) PCT Filed: Apr. 3, 2020

(86) PCT No.: PCT/US2020/026658
§ 371 (c)(1),
(2) Date: Oct. 1, 2021

(87) PCT Pub. No.: WO2020/206314
PCT Pub. Date: Oct. 8, 2020

(65) Prior Publication Data
US 2022/0168223 A1    Jun. 2, 2022

Related U.S. Application Data

(60) Provisional application No. 62/828,916, filed on Apr. 3, 2019.

(51) Int. Cl.
*A61K 9/127* (2006.01)
*A61K 9/00* (2006.01)
*A61K 31/7076* (2006.01)

(52) U.S. Cl.
CPC .......... *A61K 9/1274* (2013.01); *A61K 9/0019* (2013.01); *A61K 31/7076* (2013.01)

(58) Field of Classification Search
None
See application file for complete search history.

(56) References Cited

U.S. PATENT DOCUMENTS

| 5,814,335 A | 9/1998 | Webb et al. |
| 5,932,558 A | 8/1999 | Cronstein et al. |
| (Continued) |

FOREIGN PATENT DOCUMENTS

KR    10073710 A    7/2007

OTHER PUBLICATIONS

Carmen Corciulo et al. "Endogenous adenosine maintains cartilage homeostasis and exogenous adenosine inhibits osteoarthritis progression." Nature Communications, 8:15019 | DOI: 10.1038/ncomms15019, published May 11, 2017, pp. 1-13 + 20 pages of supplementary information. (Year: 2017).*

(Continued)

*Primary Examiner* — Isaac Shomer
(74) *Attorney, Agent, or Firm* — Hodgson Russ LLP

(57) ABSTRACT

Provided are liposomes that encapsulate adenosine. The liposomes may be formed from sphingomyelin or a combination of sphingomyelin and 1,2-dimyristoyl-sn-glycero-3-phosphocholine (DMPC) or a combination of sphingomyelin and 1,2-dimyristoyl-sn-glycero-3-phosphorylglycerol (DMPG) or a combination of sphingomyelin, DMPG, and DMPC. The liposomes encapsulating adenosine may be used to induce cartilage regeneration, treat osteoarthritis, (Continued)

Statistics: One-way (Brown-Forsythe and Welch) ANOVA, *P<0.05, P<0.01, *P<0.001 v/s vehicle, †P<0.05 v/s RgnA01 alleviate joint pain, and/or slow, arrest, and/or reverse progressive structural tissue damage associated with osteoarthritis or treat osteoarthritis, rheumatoid arthritis, acute gouty arthritis, and/or synovitis. The liposomes may release adenosine for up to two weeks.

23 Claims, 17 Drawing Sheets

(56) References Cited

U.S. PATENT DOCUMENTS

| | | | |
|---|---|---|---|
| 6,015,576 A | 1/2000 | See et al. | |
| 8,110,217 B2 | 2/2012 | Chancellor et al. | |
| 10,441,541 B2* | 10/2019 | Cronstein | A61K 31/52 |
| 10,639,278 B2 | 5/2020 | Kaufman et al. | |
| 2003/0235611 A1 | 12/2003 | Ehringer et al. | |
| 2004/0062797 A1 | 4/2004 | Loeb | |
| 2004/0082521 A1 | 4/2004 | Singh | |
| 2006/0008909 A1 | 1/2006 | Cullis et al. | |
| 2007/0031480 A1 | 2/2007 | Mayer et al. | |
| 2010/0098749 A1* | 4/2010 | Barenholz | A61K 9/0019 424/450 |
| 2010/0098753 A1* | 4/2010 | Minamino | A61P 9/10 424/450 |
| 2011/0250266 A1* | 10/2011 | Barenholz | A61K 9/127 424/450 |
| 2015/0343063 A1 | 12/2015 | Helson et al. | |
| 2016/0263031 A1* | 9/2016 | Kaufmann | A61P 13/10 |
| 2018/0036238 A1* | 2/2018 | Cronstein | A61K 31/522 |

OTHER PUBLICATIONS

Lauren C. Strazzulla & Bruce N. Cronstein. "Regulation of bone and cartilage by adenosine signaling." Purinergic Signalling, vol. 12, 2016, pp. 583-593. (Year: 2016).*

Liliana K. Bar, Yechezkel Barenholz, and Thomas E. Thompson. "Effect of Sphingomyelin Composition on the Phase Structure of Phosphatidylcholine-Sphingomyelin Bilayers." Biochemistry, vol. 36, 1997, pp. 2507-2516. (Year: 1997).*

Egerdie, R.B., et al., The Effect of Liposome Encapsulated Antineoplastic Agents on Transitional Cell Carcinoma in Tissue Culture, The Journal of Urology, Aug. 1, 1989, vol. 142, No. 2, Part 1, pp. 390-398.

Shah, J., et al., Structural and thermotropic properties of synthetic C16:0 (palmitoyl) ceramide: effect of hydration, Journal of Lipid Research, Sep. 1, 1995, vol. 36, No. 9, pp. 1936-1944.

Yatvin, M.B., et al., Design of Liposomes for Enhanced Local Release of Drugs by Hyperthermia, Science, Dec. 22, 1978, vol. 202, No. 4374, pp. 1290-1293.

Hsueh, Y-W., et al., The Effect of Ceramide on Phosphatidylcholine Membranes: A Deuterium NMR Study, Biophysical Journal, Jan. 6, 2009, vol. 82, No. 6, pp. 3089-3095.

* cited by examiner

LIPOSOMES ENCAPSULATING ADENOSINE

CROSS REFERENCE TO RELATED APPLICATIONS

This application claims priority to U.S. Provisional Application No. 62/828,916, filed on Apr. 3, 2019, the disclosure of which incorporated herein.

BACKGROUND OF THE DISCLOSURE

Osteoarthritis (OA), a disease characterized by cartilage loss and the most common type of arthritis, affects 151 million people worldwide, including nearly 10% of the population of the United States and other industrialized countries. Age, prior trauma, obesity, and genetics are among the risk factors for developing this degenerative joint disorder. The incidence of OA increases with age, and the resulting pain, loss of joint function and mobility, social isolation, and broadly reduced quality of life make OA a condition with a high medical and social impact. OA can affect any joint, but most commonly affects the knee, hip, and hand. The prevalence of OA is greatest in the knee joint, in both women (47%) and men (40%). Current treatment options are less than optimal and do not correct the underlying problem. Therapy is mostly palliative, including use of nonsteroidal anti-inflammatory drugs (e.g. ibuprofen), narcotic analgesics, exercise, and acupuncture. The FDA has also approved OA-specific treatments, including corticosteroids (anti-inflammatory agents) and hyaluronic acid (lubrication, pain relief), all of which are delivered via intraarticular (IA) injection. While these injectable agents provide symptomatic relief, none are restorative.

The purinergic system plays a critical role in maintaining cartilage homeostasis. Adenosine, acting at its A2A receptor (A2AR), is a critical autocrine homeostatic factor that maintains chondrocyte and cartilage balance. Adenosine is an endogenously produced physiological regulator, and its intracellular and extracellular concentrations are tightly controlled by oxygen consumption, cellular stress, and mitochondrial functionality. Extracellular adenosine derives mainly from hydrolysis of ATP (primarily, but not exclusively, by the ectoenzymes CD39 and CD73) and mediates its effects via activation of G-protein-coupled receptors (A1R, A2AR, A2BR, and A3R). These adenosine receptors are highly conserved evolutionarily, and their expression and function tend to be conserved as well. Adenosine has long been known to regulate inflammation and immune responses, and previous work has demonstrated the importance of adenosine and its receptors in osteoblast, osteoclast, and bone marrow homeostasis. Prior studies have suggested that adenosine receptors also regulate chondrocyte physiology and pathology in response to inflammatory stimuli in rodent, equine, bovine, and human chondrocytes, although the specific receptor(s) involved have not been identified. Removal of endogenous adenosine (by addition of adenosine deaminase) or blockade of A2AR leads to cartilage degradation in equine cartilage explants, although equine purine metabolism differs from that of other species, as adenosine deaminase, present in the lymphocytes, plasma, and extracellular fluid of most species, is not present in horse lymphocytes or serum. A3R stimulation has been reported to diminish OA development in a chemically induced model of OA, principally due to the anti-inflammatory effects of A3R agonists. However, adenosine has a half-life of mere seconds.

BRIEF SUMMARY OF DISCLOSURE

The present disclosure provides injectable formulations. Also disclosed are methods of making and using the injectable formulations. The injectable formulations comprise liposomes and saline, where the liposomes are metastable and encapsulate adenosine.

BRIEF DESCRIPTION OF THE FIGURES

For a fuller understanding of the nature and objects of the disclosure, reference should be made to the following detailed description taken in conjunction with the accompanying figures.

DETAILED DESCRIPTION OF THE DISCLOSURE

Figure 1:
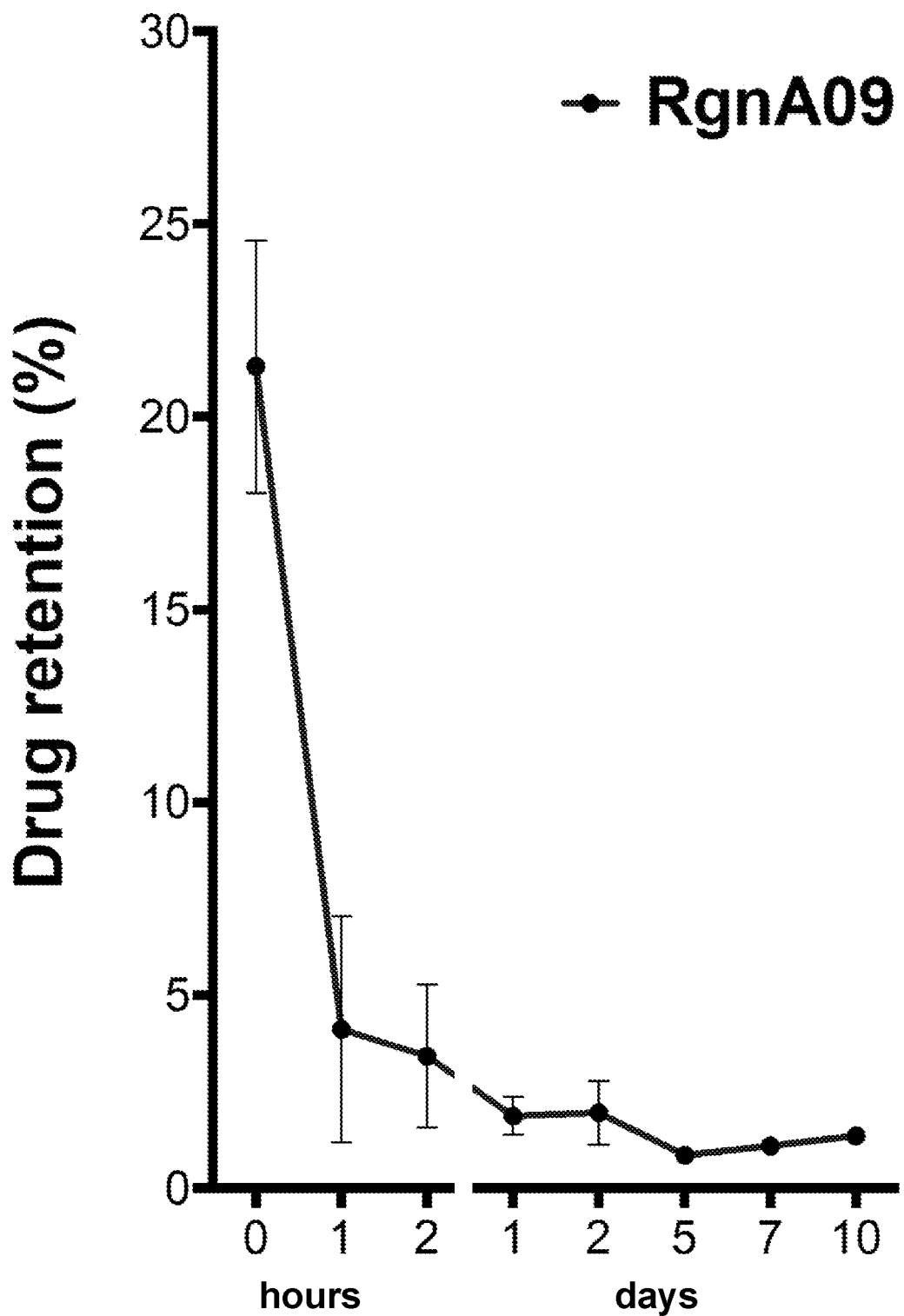
FIG. 1 shows adenosine retention of liposomes formed from RgnA09.
Figure 2:
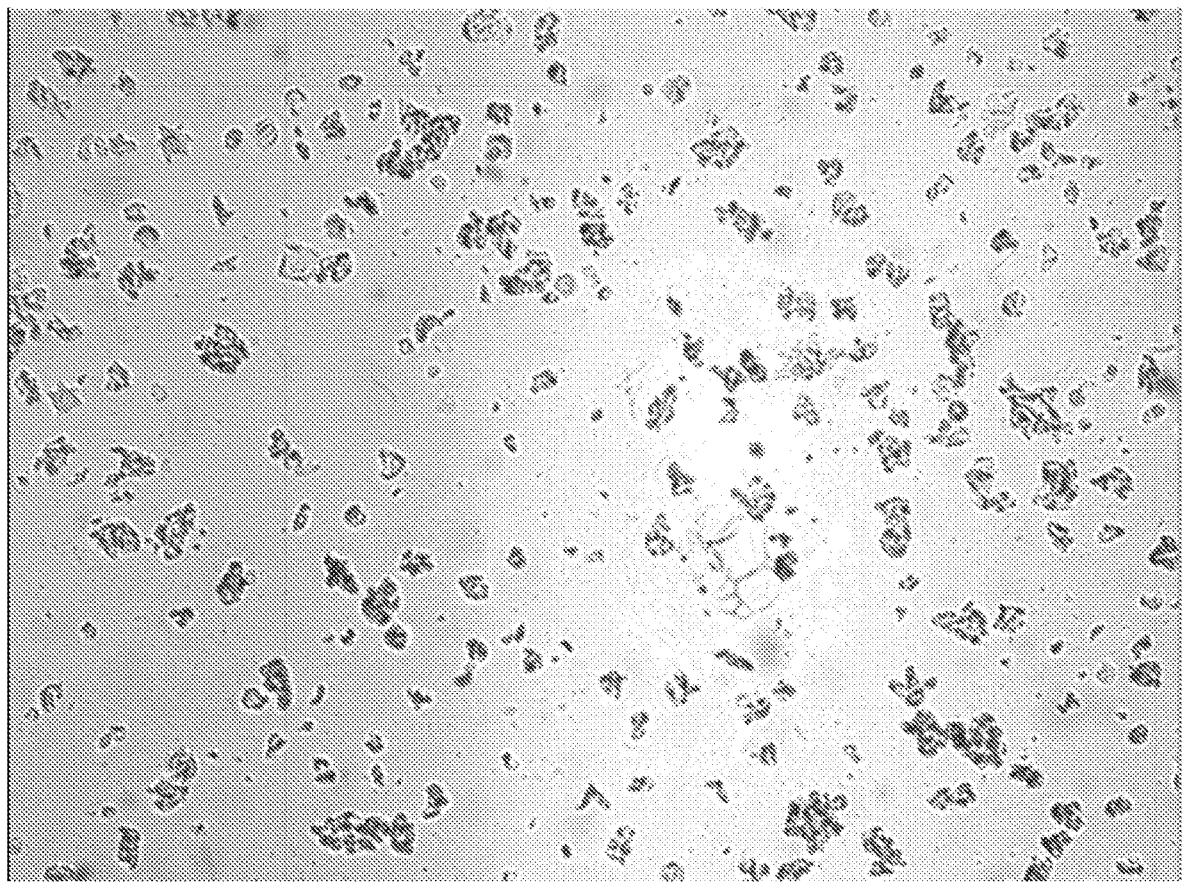
FIG. 2 shows a microscopy image of a liposomal suspension formed from RgnA09.
Figure 3:
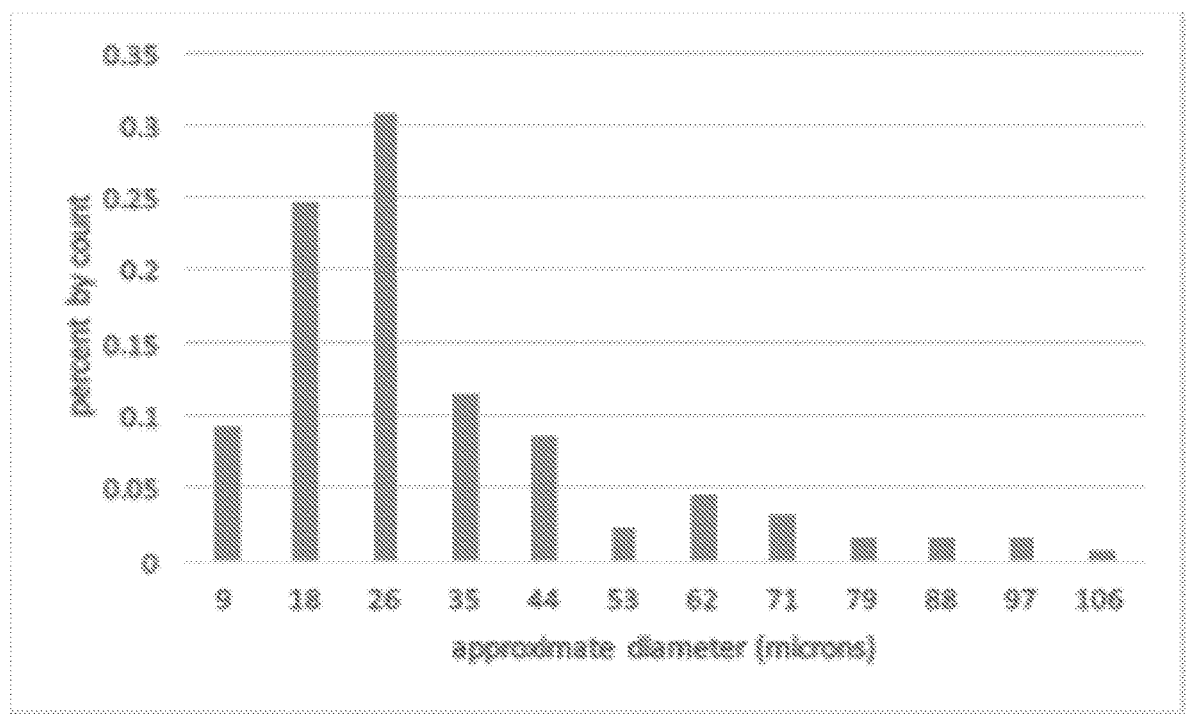
FIG. 3 shows a histogram of the approximate diameter of liposomes formed from RgnA09.

Although claimed subject matter will be described in terms of certain embodiments, other embodiments, including embodiments that do not provide all of the benefits and features set forth herein, are also within the scope of this disclosure. Various structural, logical, and process step changes may be made without departing from the scope of the disclosure.

All ranges provided herein include all values that fall within the ranges to the tenth decimal place, unless indicated otherwise.

The present disclosure provides injectable formulations. Also disclosed are methods of making and using the injectable formulations.

In an aspect, the present disclosure provides injectable formulations comprising liposomes and saline, where the liposomes encapsulate adenosine.

Liposomes may comprise i) sphingomyelin or ii) sphingomyelin and 1,2-dimyristoyl-sn-glycero-3-phosphocholine (DMPC) or iii) a combination of sphingomyelin and 1,2-dimyristoyl-sn-glycero-3-phosphorylglycerol (DMPG) or iv) a combination of sphingomyelin, DMPG, and DMPC. In various examples, the liposomes comprise 70 to 100% by mass sphingomyelin. Liposomes comprising less than 100% by mass sphingomyelin may further comprise up to 30% by mass (e.g., the remainder) DMPC or DMPG or a combination of DMPC and DMPG together. In an embodiment, liposomes may comprise 70 to 99.9% by mass sphingomyelin and 0.1 to 30% by mass (e.g., the remainder) DMPC or 1,2-dimyristoyl-sn-glycero-3-phosphorylglycerol (DMPG) or a combination of DMPC and DMPG together. In an embodiment, liposomes comprise 75 to 100% by mass sphingomyelin. Liposomes comprising less than 100% by mass sphingomyelin may further comprise up to 25% by mass (e.g., the remainder) DMPC or DMPG or DMPC and DMPG together. In an embodiment, liposomes comprise 75 to 99.9% by mass sphingomyelin and from 0.1 to 25% by mass (e.g., the remainder) DMPC or DMPG or DMPC and DMPG together. For example, liposomes may comprise 75, 80, 85, 90, 95, 96, 97, 98, 99, and 99.9% sphingomyelin and the remainder is DMPC, DMPG, or a combination thereof. The percent by mass refers to the total mass of phospholipids.

Liposomes may have a diameter and/or mean diameter of 50 nm to 150 μm, including all 0.1 nm values and ranges therebetween (e.g., 50 nm to 1 μm, 50 nm to 750 μm, 50 to 500 nm, 50 to 250 nm, 50 to 100 nm, 100 nm to 1 μm, 100 to 750 nm, 100 to 500 nm, 100 to 250 nm, 1 to 150 μm, 1 to 100 μm, 1 to 50 μm, 1 to 40 μm, 1 to 30 μm, 1 to 25 μm, 1 to 20 μm, 1 to 10 μm, 1 to 5 μm). For example, liposomes may have a diameter and/or mean diameter of 50 nm, 75 nm, 100 nm, 250 nm, 500 nm, 1 μm, 10 μm, 25 μm, 30 μm, 40 μm, 50 μm, 75 μm, or 100 μm. In an embodiment, at least 60, at least 70, at least 80, at least 90, at least 95, at least 96, at least 97, at least 98, at least 99, at least 99.9, or 100% of the liposomes have a diameter in the range of 50 nm to 1 μm, 50 nm to 750 μm, 50 to 500 nm, 50 to 250 nm, 50 to 100 nm, 100 nm to 1 μm, 100 to 750 nm, 100 to 500 nm, 100 to 250 nm, 1 to 150 μm, 1 to 100 μm, 1 to 50 μm, 1 to 40 μm, 1 to 30 μm, 1 to 25 μm, 1 to 20 μm, 1 to 10 μm, 1 to 5 μm. In an embodiment, there are no liposomes having a diameter greater than 150 μm. In an embodiment, less than 1% of the liposomes have a diameter greater than 150 μm. In various embodiments, a liposome may be produced by the ethanol injection method and the resulting liposomes may be smaller than liposomes formed by other methods.

Prior to release of adenosine, the liposomes of the present disclosure may be metastable. Metastable liposomes provide enhanced delivery due to greater stability at the site of delivery. Metastable liposomes a) have a relative diameter different than 1 (e.g., the metastable liposome does not have a perfectly circular or spherical shape); b) are large enough such that the expansive stress associated with membrane bending is not strong enough to overcome the liposome's tendency toward conformational equilibrium; and c) have a longest linear dimension (e.g., diameter) of 100 nm to 150 μm, including every 0.1 nm value and range therebetween. Such liposomes collapse (e.g., constrict or contract) into a smaller stable form when subjected to a temperature (e.g., in contact with a reservoir having a temperature) of 35-45° C., including all 0.1° C. value and range therebetween (e.g., 35, 36, 37, 38, 39, 40, 41, 42, 43, 44, or 45° C.) (e.g., about (or slightly higher than) 40° C.). In an embodiment, smaller stable liposomes have a longest linear dimension (e.g., diameter) of 50 nm to 110 μm, including every 0.1 nm value and range therebetween. Additionally, the ratio of the volume enclosed by the liposomes at 25° C. relative to the volume enclosed by the liposomes following heating to a temperature that surpasses the gel-fluid phase transition of one or more lipids forming the liposomes is greater than 10. Metastable liposomes that contain a hydrophilic agent may collapse at 35-45° C., including all 0.1° C. value and range therebetween (e.g., 35, 36, 37, 38, 39, 40, 41, 42, 43, 44, or 45° C.) (e.g., approximately 40° C.) to release (e.g., gradually release) their payload (e.g., adenosine) upon such collapse (e.g., contraction or constriction). Metastable liposomes are described in U.S. Pat. Pub. No. 2016/0263031 (relevant portions of which are hereby incorporated by reference). Metastable liposomes may be referred to simply as liposomes.

The liposomes may be formulated with one or more excipients. The formulations can be in the form of a liquid or gel, preferably a liquid, for injectable application.

Liposomes are formed from one or more lipids, which can be neutral, anionic, or cationic at physiologic pH. Examples of types of lipids include, but are not limited to, sterols and lipids such as cholesterol, phospholipids, lysolipids, lysophospholipids, sphingolipids or PEGylated lipids. In an embodiment, the carbon chain length of the phospholipids is $C_{10}$ to $C_{22}$ length. In an embodiment, the carbon chain length of the phospholipids is $C_{14}$ to $C_{20}$. Suitable lipids include, but are not limited to, phosphatidylcholine (PC) (such as egg PC, soy PC) and phosphatidylglycerols. Examples of PCs include, such as, for example, 1,2-dioleoylphosphatidylcholine (DOPC), 1,2-distearoyl phosphatidylcholine (DSPC), 1,2-dipalmitoyl phosphatidylcholine (DPPC), and 1,2-dimyristoyl phosphatidylcholine (DMPC). Various phosphatidylglycerols may be used. Non-limiting examples of phosphatidylglycerols include 1,2-dioleoyl phosphatidylglycerol (DOPG), 1,2-distearoyl phosphatidylglycerol (DSPG), 1,2-dipalmitoyl phosphatidylglycerol (DPPG), and 1,2-dimyristoyl-sn-glycero-3-phosphorylglycerol (DMPG).

In an embodiment, the phospholipids are sphingomyelin, or sphingomyelin with DMPC or DMPG, or a combination thereof. The total lipid concentration may be 7 to 12 mg/mL, including all 0.01 mg/mL values and ranges therebetween. In an embodiment, the total lipid concentration is 8 to 10 mg/mL. In an embodiment, the total lipid concentration is 8 mg/mL or 10 mg/mL. In an embodiment where the liposome comprises sphingomyelin, DMPC, and DMPG, the ratio of DMPC to DMPG is 6 to 4 to 8 to 2. In an embodiment, the ratio of DMPC to DMPG is 7 to 3.

The liposomes have an aqueous compartment. The aqueous compartment can contain water and adenosine. The concentration of adenosine may be 0.1 to 7 mg/mL, including all 0.01 mg/mL values and ranges therebetween. In an embodiment, the concentration of adenosine may be 0.1 to 4 mg/mL. In an embodiment, the concentration of adenosine is 3 mg/mL.

Methods of manufacturing metastable liposomes are described herein. In an embodiment, dehydrated metastable liposomes are prepared from a homogenous dispersion of a phospholipid, preferably sphingomyelin, in a water/tert-butyl alcohol (TBA) co-solvent system at a ratio of 2:1 mg phospholipid to mL water/TBA. Various ratios of water to TBA may be used (e.g., 10:1, 9:1, 8:1:7:1, 6:1, 5:1. 4:1, 3:1, 2:1, 9:2, 7:2, 5:2, 3:2, 10:3, 8:3, 7:3, 5:3 (water:TBA)). The isotropic monophasic solution of liposomes is freeze dried to generate dehydrated liposomal powder in a sterile vial. The freeze drying step leaves empty lipid vesicles or dehydrated liposomes after removing both water and TBA from the vial. On addition of a pharmaceutically acceptable carrier, such as water, physiological saline or PBS, the lyophilized product spontaneously forms a large, metastable liposome dispersion. The ratio of lipid to TBA is an important factor affecting the size and the polydispersity of resulting liposome preparation.

In an embodiment, dehydrated metastable liposomes, such as, for example, RgnA09, are prepared from a solution comprising a dispersion of a plurality of phospholipids in a TBA/water co-solvent system having a 1:1 ratio by volume of water to TBA. For example, for a solution comprising 100 mg of phospholipids, 1-50 mL (e.g., 1, 2, 3, 4, 5, 6, 7, 8, 9, 10, 20, 25, 30, 40, or 50 mL) of a 1:1 ratio by volume of TBA:water co-solvent system is used. The plurality of phospholipids may be a mixture of 75% sphingomyelin (by mass) and a 25% PC/PG mixture (by mass), where the PC/PG mixture comprises 70% (by mass) DMPC and 30% (by mass) DMPG (e.g., of the total plurality of phospholipids comprising sphingomyelin and the PC/PG mixture, 70% (by mass) of the plurality of phospholipids is sphingomyelin, 17.5% (by mass) of the plurality of phospholipids is DMPC, and 7.5% (by mass) is DMPG). The resulting solution comprising the plurality of phospholipids is freeze dried to generate a dehydrated liposomal powder in a sterile vile. The lyophilate (e.g., the dehydrated liposomal powder) may then be rehydrated with a solution comprising adenosine (e.g., for 100 mg phospholipids, 10 mL of an aqueous solution comprising adenosine (e.g., a saline solution comprising adenosine, where the adenosine has a concentration of 0.1 to 7 mg/mL (e.g., 3 mg/mL)) is used to rehydrate the lyophilate).

In an embodiment, dehydrated metastable liposomes, such as, for example, RgnA10, are prepared from a solution comprising a dispersion of phospholipid in a TBA/water co-solvent system having a 3:2 ratio by volume of water to TBA. For example, for a solution comprising 100 mg of phospholipids, 1-50 mL (e.g., 1, 2, 3, 4, 5, 6, 7, 8, 9, 10, 20, 25, 30, 40, or 50 mL) of a 3:2 ratio by volume of water:TBA co-solvent system is used. The phospholipid may be sphingomyelin. The resulting solution comprising the phospholipid is freeze dried to generate a dehydrated liposomal powder in a sterile vial. The lyophilate (e.g., the dehydrated liposomal powder) may then be rehydrated with a solution comprising adenosine (e.g., for 100 mg phospholipids, 10 mL of an aqueous solution comprising adenosine (e.g., a saline solution comprising adenosine, where the adenosine has a concentration of 0.1 to 7 mg/mL (e.g., 3 mg/mL)) is used to rehydrate the lyophilate).

Various methods may be used to manufacture liposomes of the present disclosure. For example, methods to manufacture include, but are not limited to, the emulsion method, the reverse-phase evaporation method, the detergent depletion method, and the ethanol injection method. Various other methods are known in the art and are encompassed within the scope of this disclosure.

Liposomal-adenosine suspensions may be prepared by methods of the present disclosure. The dehydrated liposomal powder is hydrated via addition of an adenosine solution and then mixed. For example, 10 mL of an adenosine solution (e.g., 3 mg/mL adenosine solution in saline (e.g., 0.9% by mass sodium chloride (9 mg of NaCl per mL of water)) is added to a vial containing 100 mg of the dehydrated liposomal powder. The resulting liposomes comprising adenosine may be multilamellar. The liposomes comprising adenosine may have a longest linear dimension (e.g., diameter) of 50 nm to 150 μm, including all 0.1 nm values and ranges therebetween (e.g., 50 nm to 1 μm, 50 nm to 750 μm, 50 to 500 nm, 50 to 250 nm, 50 to 100 nm, 100 nm to 1 μm, 100 to 750 nm, 100 to 500 nm, 100 to 250 nm, 1 to 150 μm, 1 to 100 μm, 1 to 50 μm, 1 to 40 μm, 1 to 30 μm, 1 to 25 μm, 1 to 20 μm, 1 to 10 μm, 1 to 5 μm).

The selected dosage depends upon the desired therapeutic effect, on the route of administration, and on the duration of the treatment desired. Generally dosage levels of 0.001 to 10 mg/kg of body weight daily are administered to mammals (e.g., individuals). Generally, for intravenous injection or infusion, dosage may be lower.

Compositions may also be administered orally, by parenteral (intramuscular, intraperitoneal, intravenous (IV) or subcutaneous injection), transdermal (either passively or using iontophoresis or electroporation), or transmucosal (nasal, vaginal, rectal, or sublingual) routes of administration and can be formulated in dosage forms appropriate for each route of administration. In an embodiment, the formulation is injected directly into the joint of an individual.

Metastable liposomes containing adenosine of the present disclosure have several advantages. For example, the metastable liposomes have slow release of the adenosine, thus extending the biological activity of the delivered adenosine and/or reduce the dosage required.

Different size dosage units of the metastable liposomal formulation may be used. A dosage unit containing a dry powder of dehydrated metastable pre-liposomal lyophilate or an aqueous solution of adenosine or other hydrophilic active agent can be reconstituted in a container with a pharmaceutically acceptable carrier. Preferably, the pharmaceutically acceptable carrier is an aqueous carrier. Suitable amounts of dosage units include, but are not limited to, 0.1-1 mg, 1-3 mg, 3-10 mg, 10-20 mg and 20-50 mg. Suitable concentrations of dosage units include, but are not limited to, 0.05 mg/mL to 10 mg/mL, preferably 0.05 mg/mL to 5 mg/mL, more preferably 0.05 mg/mL to 3.5 mg/mL.

The injectable formulations of the present disclosure may be used to induce cartilage regeneration, treat osteoarthritis, alleviate joint pain, and/or slow, arrest, and/or reverse progressive structural tissue damage associated with osteoarthritis in an individual in need of treatment. In an example, the individual may have or be suspected of having osteoarthritis, rheumatoid arthritis, acute gouty arthritis, and/or synovitis. A method to induce cartilage regeneration, treat osteoarthritis, alleviate joint pain, and/or slow, arrest, and/or reverse progressive structural tissue damage associated with osteoarthritis in an individual in need of treatment comprises administering to the individual in need of treatment an injectable formulation of the present disclosure.

In various embodiments, an individual is a human or non-human mammal. Examples of non-human mammals include, but are not limited to, agricultural animals (e.g., farm animals), such as cows, hogs, sheep, and the like, as well as pet, service, or sport animals such as horses, dogs, cats, and the like. Additional non-limiting examples of individuals include rabbits, rats, and mice.

Upon administration to an individual in need of treatment, adenosine is released from the liposomes for up to two weeks. In an embodiment, following administration of the injectable formulation, adenosine is released from the liposomes within 1 second to 1 hour (e.g., 1 minute to 1 hour) of administration to the individual. In an embodiment, at least a portion of the adenosine (e.g., 1 to 20% of the adenosine) is released from the liposomes within 1 minute to 1 hour of administration to the individual. In an embodiment, at least a portion of the adenosine (e.g., 1 to 20% of the adenosine) is released within 1 second, 5 seconds, 10 seconds, 20 seconds, 30 seconds, 40 seconds, 50 seconds, 1 minute, 2 minutes, 3 minutes, 4 minutes, 5 minutes, or 10 minutes of administration the individual.

The injectable formulation may be administered via intra-articular injection to a joint of the individual. The injectable formulation may be administered in one or more injections. The formulations may be administered multiple times (e.g., up to ten times), such as, for example, once every 10 days or longer.

The steps of the method described in the various embodiments and examples disclosed herein are sufficient to carry out the methods of the present disclosure. Thus, in an embodiment, the method consists essentially of a combination of the steps of the methods disclosed herein. In an embodiment, the method consists of such steps.

The following Statements describe various non-limiting examples of the present disclosure:

Statement 1. A formulation (e.g., an injectable formulation) comprising saline and one or more liposomes, wherein the one or more liposomes comprise one or more lamellae (e.g., one or more multilamellar liposomes), wherein the liposome lamellae comprise 70 to 100% by mass sphingomyelin and when there is less than 100% by mass sphingomyelin the remainder is (e.g., up to 30% by mass) 1,2-dimyristoyl-sn-glycero-3-phosphocholine (DMPC) or 1,2-dimyristoyl-sn-glycero-3-phosphorylglycerol (DMPG) or DMPC and DMPG together, where the liposomes (a) have a diameter of 50 nm to 150 µm, including all 0.1 nm values and ranges therebetween (e.g., (e.g., 50 nm to 1 µm, 50 nm to 750 µm, 50 to 500 nm, 50 to 250 nm, 50 to 100 nm, 100 nm to 1 µm, 100 to 750 nm, 100 to 500 nm, 100 to 250 nm, 1 to 150 µm, 1 to 100 µm, 1 to 50 µm, 1 to 40 µm, 1 to 30 µm, 1 to 25 µm, 1 to 20 µm, 1 to 10 µm, 1 to 5 µm); and (b) encapsulate adenosine in the aqueous compartment of the liposome. One or more of the liposomes have a diameter of 50 nm to 100 µm. One or more of the liposomes have a diameter of 100 nm to 150 µm.

Statement 2. A formulation (e.g., an injectable formulation) according to Statement 1, where the liposomes are metastable.

Statement 3. A formulation (e.g., an injectable formulation) according to Statement 1, where the adenosine or a portion thereof is released for up to two weeks or upon administration to a joint of an individual, the adenosine or a portion thereof is released for up to two weeks.

Statement 4. A formulation (e.g., an injectable formulation) according to any one of the preceding Statements, further comprising an excipient.

Statement 5. A formulation (e.g., an injectable formulation) according to any one of the preceding Statements, where the adenosine concentration is 0.1 to 7 mg/mL.

Statement 6. A formulation (e.g., an injectable formulation) according to Statement 5, where the adenosine concentration is 0.1 to 4 mg/mL.

Statement 7. A formulation (e.g., an injectable formulation) according to any one of the preceding Statements, where the ratio of DMPC and DMPG is from 6 to 4 to 8 to 2.

Statement 8. A formulation (e.g., an injectable formulation) according to Statement 7, where the ratio of DMPC and DMPG is 7 to 3.

Statement 9. A formulation (e.g., an injectable formulation) according to any one of the preceding Statements, where the total lipid concentration is 7 to 12 mg/mL.

Statement 10. A formulation (e.g., an injectable formulation) according to any one of the preceding Statements, where the liposomes collapse (e.g., contract or constrict) at a temperature of 35-45° C., including all 0.1° C. value and range therebetween (e.g., 35, 36, 37, 38, 39, 40, 41, 42, 43, 44, or 45° C.) (e.g., approximately 40° C. to release their payload).

Statement 11. A formulation (e.g., an injectable formulation) according to any one of the preceding Statements, where adenosine is released within 1 second to 1 hour of administration (e.g., within 1 minute to 1 hour) to the joint of the individual.

Statement 12. A formulation (e.g., an injectable formulation) according to Statement 11, where at least a portion of the adenosine is released within 1 second to 1 hour of administration (e.g., within 1 minute to 1 hour) to the joint of the individual.

Statement 13. A formulation (e.g., an injectable formulation) according to Statement 11 or Statement 12, where at least 1 to 20% of the adenosine is released 1 second to 1 hour of administration (e.g., within 1 minute to 1 hour) to the joint of the individual.

Statement 14. A formulation (e.g., an injectable formulation) according to any one of Statements 11-13, where the at least a portion of the adenosine or the at least 1 to 20% of adenosine is released within 1 second, 5 seconds, 10 seconds, 20 seconds, 30 seconds, 40 seconds, 50 seconds, 1 minute, 2 minutes, 3 minutes, 4 minutes, 5 minutes or 10 minutes of administration to the joint of the individual.

Statement 15. A method of inducing cartilage regeneration and/or treating osteoarthritis in an individual in need of treatment, comprising administering to the individual the formulation (e.g., injectable formulation) according to any one of the preceding Statements.

Statement 16. A method of alleviating joint pain in an individual in need of treatment, comprising administering to the individual the formulation (e.g., injectable formulation) according to any one of Statements 1-14.

Statement 17. A method of slowing, arresting, and/or reversing progressive structural tissue damage associated with osteoarthritis in an individual in need of treatment, comprising administering to the individual the formulation (e.g., injectable formulation) according to any one of Statements 1-14.

Statement 18. A method according to any one of Statements 15-17, where the formulation (e.g., injectable formulation) is administered via intra-articular injection to a joint of the individual.

Statement 19. A method according to any one of Statements 15-18, where the injectable formulation is administered in one or more injections.

Statement 20. A method according to any one of Statements 15-19, where the injectable formulation is administered multiple times (e.g., up to 10 times) once every 10 days.

Statement 21. A method according to any one of Statements 15-20, where the individual has osteoarthritis, rheumatoid arthritis, acute gouty arthritis, and/or synovitis.

Statement 22. A method according to any one of Statements 15-21, where the individual is a human or non-human mammal. Examples of non-human mammals include, but are not limited to, agricultural animals (e.g., farm animals), such as cows, hogs, sheep, and the like, as well as pet, service, or sport animals such as horses, dogs, cats, and the like. Additional non-limiting examples of individuals include rabbits, rats, and mice.

The following examples are presented to illustrate the present disclosure. They are not intended to be limiting in any matter.

Example 1

This example provides a description of liposomes of the present disclosure.

Because adenosine has a half-life of mere seconds, the liposomal-adenosine used for the above research was made fresh daily. A series of shelf-stable formulation options based on lipid constituents, solubility efficiency and retention properties were developed and evaluated. It was determined if cholesterol/stabilizing agents should be included, and optimized the variables. The percentage of liposomal-bound adenosine in the total formulation, which can be increased or reduced by reducing or increasing the amount of adenosine solution used to hydrate the fixed amount of pre-liposomal lyophilate, was measured. The fraction of adenosine versus (adenosine+lipid) in the resulting pellet of the liposomes that form from hydrating the pre-liposomal lyophilate with the adenosine solution is dependent on the concentration of adenosine in the solution not the volume used.

All formulations hydrated with water containing 7 mg/ml of Adenosine.

| Formulations | Conditions | | | | | |
| --- | --- | --- | --- | --- | --- | --- |
| | RgnA02 | RgnA03 | RgnA04 | RgnA05 | RgnA06 | RgnA07 |
| mg lipid | 400 | 300 | 200 | 100 | 125 | 80 |
| % SM | 0% | 25% | 50% | 75% | 75% | 100% |
| % PC/PG Mixture | 100% | 75% | 50% | 25% | 25% | 0% |
| % DMPC | 70.0% | 52.5% | 35.0% | 17.5% | 17.5% | 0.0% |
| % DMPG | 30.0% | 22.5% | 15.0% | 7.5% | 7.5% | 0.0% |
| SM (mg) | 0.00 | 75.00 | 100.00 | 75.00 | 93.75 | 80.00 |
| DMPC (mg) | 280.00 | 157.50 | 70.00 | 17.50 | 21.88 | 0.00 |
| DMPG (mg) | 120.00 | 67.50 | 30.00 | 7.50 | 9.38 | 0.00 |
| Hydrated with ADO Soln (ml) | 10 | 10 | 10 | 10 | 10 | 10 |
| Lipid in solution (mg/ml) | 40 | 30 | 20 | 10 | 12.5 | 8 |

| | data analysis | | | | | |
| --- | --- | --- | --- | --- | --- | --- |
| [lipid] mg/ml | — | 30 | 20 | 10.0 | 12.5 | 8.0 |
| lipid amount | — | 92.4 | 36.4 | 30.8 | 53.8 | ** |
| bound ADO amount | — | 5.2 | 5.0 | 5.2 | 16.6 | ** |
| ADO/lipid in pellet | — | 6% | 14% | 17% | 31% | 18% |
| pellet/total suspension | — | 24% | 39% | 24% | 55% | |
| Dissolution time & diluent volume | Took 20 mL and more time to dissolve | More than 10 mL to dissolve. Eventually didn't dissolve. | Overnight dissolution. | Dissolved in less than 5 min. | Overnight dissolution. | Dissolved in less than 5 min. |

Two formulations, RgnA09 (75% sphingomyelin, 17.5% DMPC, 7.5% DMPG) and RgnA10(100% sphingomyelin) where tested in order to assess their ability to incorporate and release adenosine over time. Liposome were formed in sterile glass vials containing 100 mg of phospholipid powder. Liposomes were mixed with 10 mL of sterile adenosine solution (3 mg/ml, in saline) provided in pre-filled plastic syringes. Samples of the Lipo-adenosine suspension (100 µL) were incubated in phosphate buffer saline for 0, 1 hour, 2 hours, 1 day and 2, 5, 7, 10 days at 37° C. At the end of each incubation time, samples where centrifuged at 23,000 g for 15 min at 4° C. Supernatant was removed and the liposome pellet was re-suspended in a saline solution containing 0.5% Triton-X100. Adenosine concentration in the remaining intact liposomes was quantified by High Performance Liquid Chromatography (HPLC).

Figure 4:
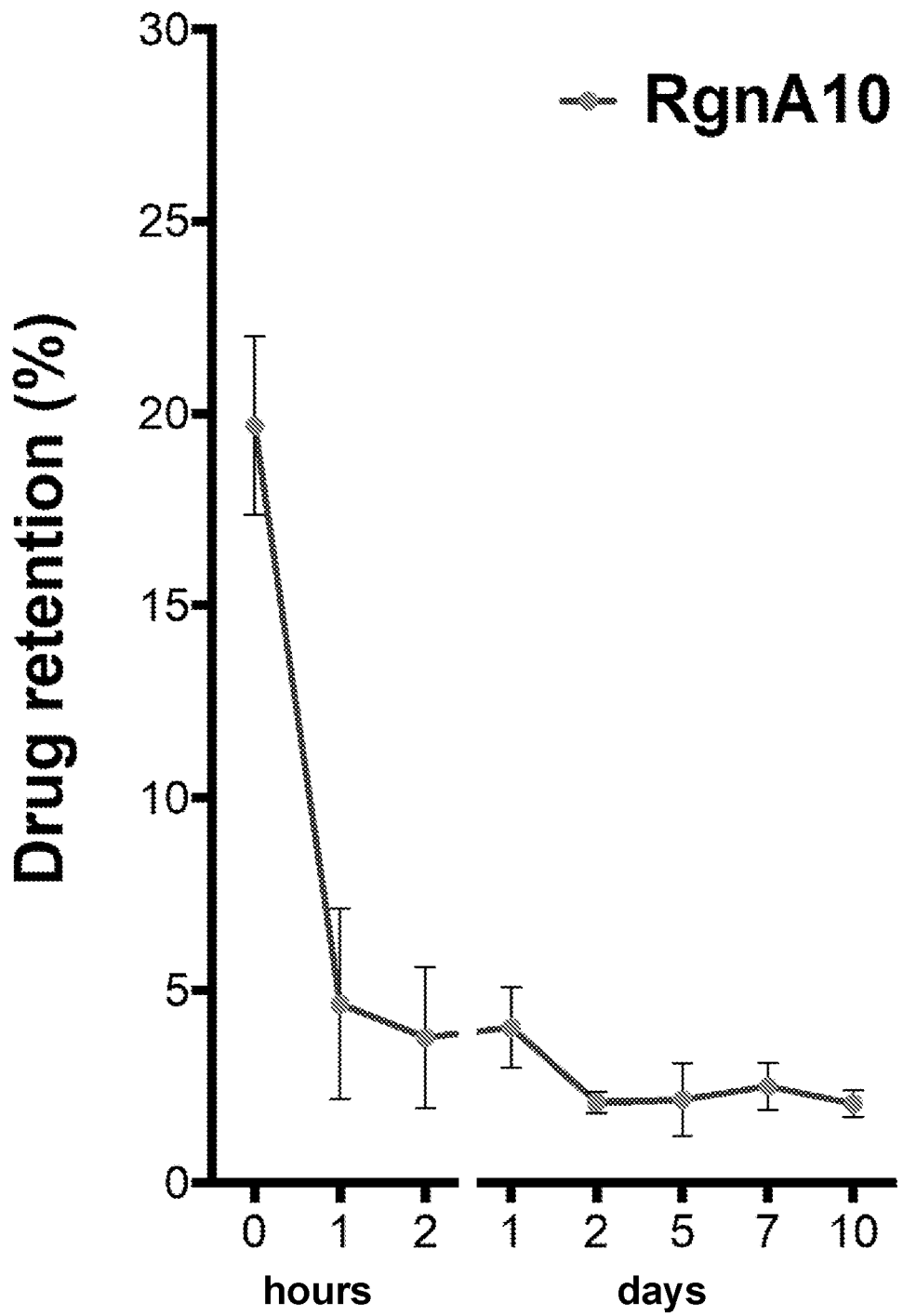
FIG. 4 shows adenosine retention of liposomes formed from RgnA10.

FIGS. 1 and 4 show the percentage of adenosine retention in both liposomal formulations. No significant difference has been detected between the RgnA09 and RgnA10. A slight higher retention was observed at time-point zero, and an increase of retention at the longer time point for the RgnA09. Freshly prepared liposome suspension (time 0) showed a retention of adenosine of 21% and 19% respectively for RgnA09 and RgnA10. The retention percentage after 1 hour of incubation drop at 4% for both formulations and slowly decrease over time reaching 1.4% and 2% (RgnA09 and RgnA10 respectively) at day 10, corresponding at 159 µM and 227 µM of adenosine.

These results show that both liposomal formulations are a good reservoir for encapsulation and slow release of adenosine in concentrations sufficient to activate A2A adenosine receptor in vivo.

The pre-liposomal lyophilate that can be rehydrated in a concentrated solution of a hydrophilic pharmacologic agent such as adenosine. In the process of said rehydration, multi-lamellar liposomal particles are created that contain said hydrophilic agent in the liposome's aqueous compartment. Said particles are "large," approximately 30 microns and are meta-stable such that they collapse into a dense form in a hyperthermic environment, approximately 40° C. Otherwise, these particles effectuate a sustained release of said pharmacologic agent if when constrained to a local closed compartment, such as within the bursa of the synovial joint of a human knee. Therefore, contained the hydrophilic agent is protected from catabolic enzymes within the physiologic environment.

The pre-liposomal lyophilate that produces these large metastable multilamellar lipid particles can be manufactured by dissolving lipids (including at least 50% sphingomyelin) and up to 50% non-sphingolipid phosphatidyl choline in a mixture of water-tertiary butyl alcohol (60:40 v/v) prior to lyophilization. 1,2-dimyristoyl-sn-glycero-3-phosphocholine (DMPC) and 1,2-Dimyristoyl-sn-glycero-3-phosphorylglycerol (DMPG) were used as the non-sphingolipids in a ratio of 70% to 30%.

Example 2

This example provides a description of liposomes of the present disclosure.

Figure 8:
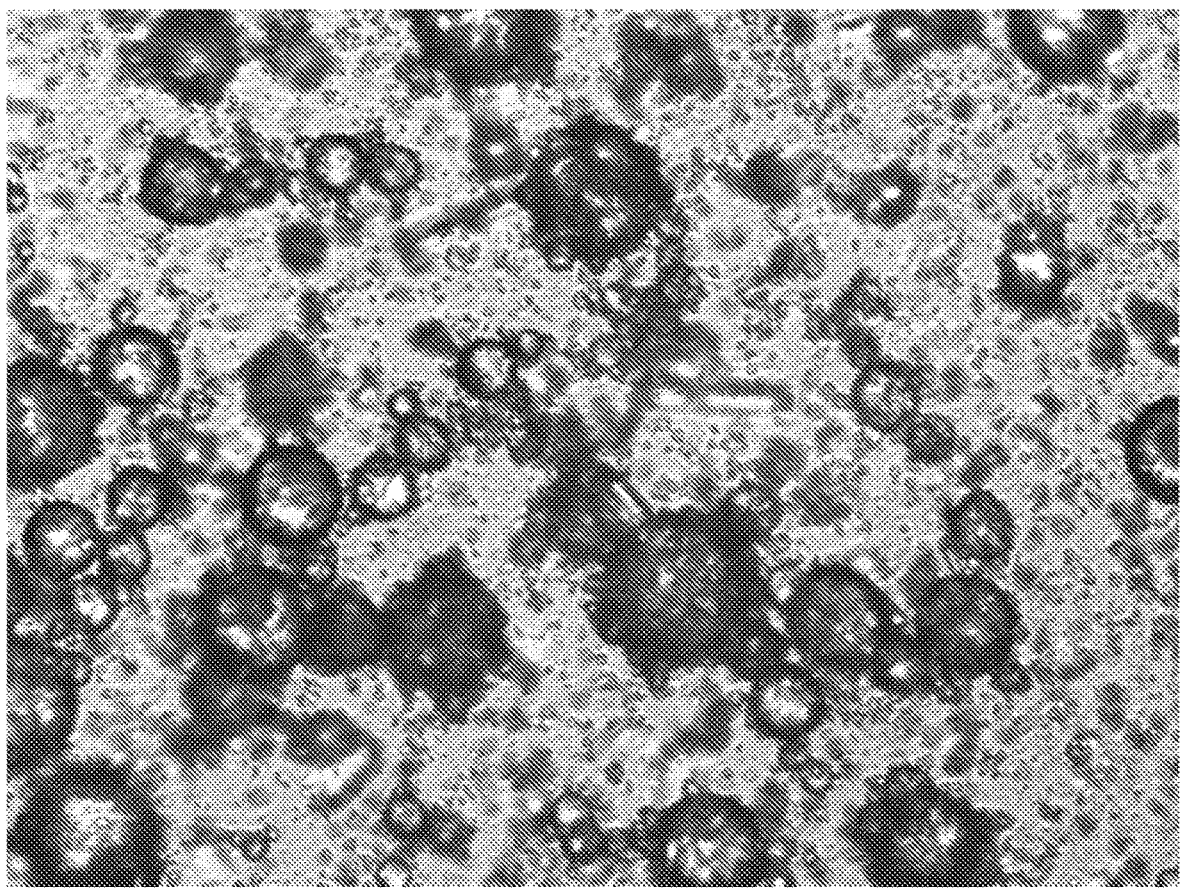
FIG. 8 shows a microscopy image of prior art liposomal suspensions. The liposomal suspension contains evidence of significant crystalized adenosine and it is believed the spherical objects are oil.

The laboratory formulations of liposomal-adenosine provided were analyzed using cross-polarized microscopy. These results are shown in FIG. 8.

The liposomal suspension, when observed microscopically, displayed evidence of significant crystalized adenosine. It is considered that this liposomal suspension may not contain significant liposomal content and is predominantly an emulsion. The spherical objects in the image are likely oil. The ingredients of this formulation contained a significant percentage (60%) of soybean oil, which would not be a component of a liposome formulation, but would be a component of an emulsion.

The solubility of adenosine in water was considered, which is 7 mg/mL. The laboratory formulation required 300 mg of adenosine to be added to 10 mL of saline. Presumably, only 70 mg of the adenosine would dissolve, leaving 230 mg of adenosine in crystalline form. It is considered that much of the pellet, when subjecting the emulsion to centrifugation, is likely to be crystalline adenosine. The pellet of the provided formulation was not by HPLC, because each time the pellet was washed, it would reduce in size until there was nothing left. The publication where this formulation was used was reviewed, and only the supernatant was analyzed by HPLC. That publication stated 73% of adenosine was retained in the liposomes. However, the amount in the pellet was inferred by measuring the concentration of adenosine in the supernatant. However, this HPLC measurement of the supernatant is consistent with 70 mg of adenosine dissolving in 10 mL of saline by its maximum solubility in water, and the remaining 230 mg of adenosine crystalized in the pellet. Presumably there are some liposomes formed with adenosine, but their presence is uncertain in this formulation.

Figure 7:
FIG. 7 shows a pre-liposomal lyophilate.

The analysis of a pre-liposomal lyophilate technique was resumed for preparing liposomal adenosine to explore the amount of adenosine capture. The advantage of this technique is that it is a stable and sterile process, ideal for pharmaceutical preparation. This technique involves the reconstitution of the sterile pre-liposomal lyophilate in the presence of the active agent. A photograph of the pre-liposomal lyophilate is shown in FIG. 7.

Figure 5:
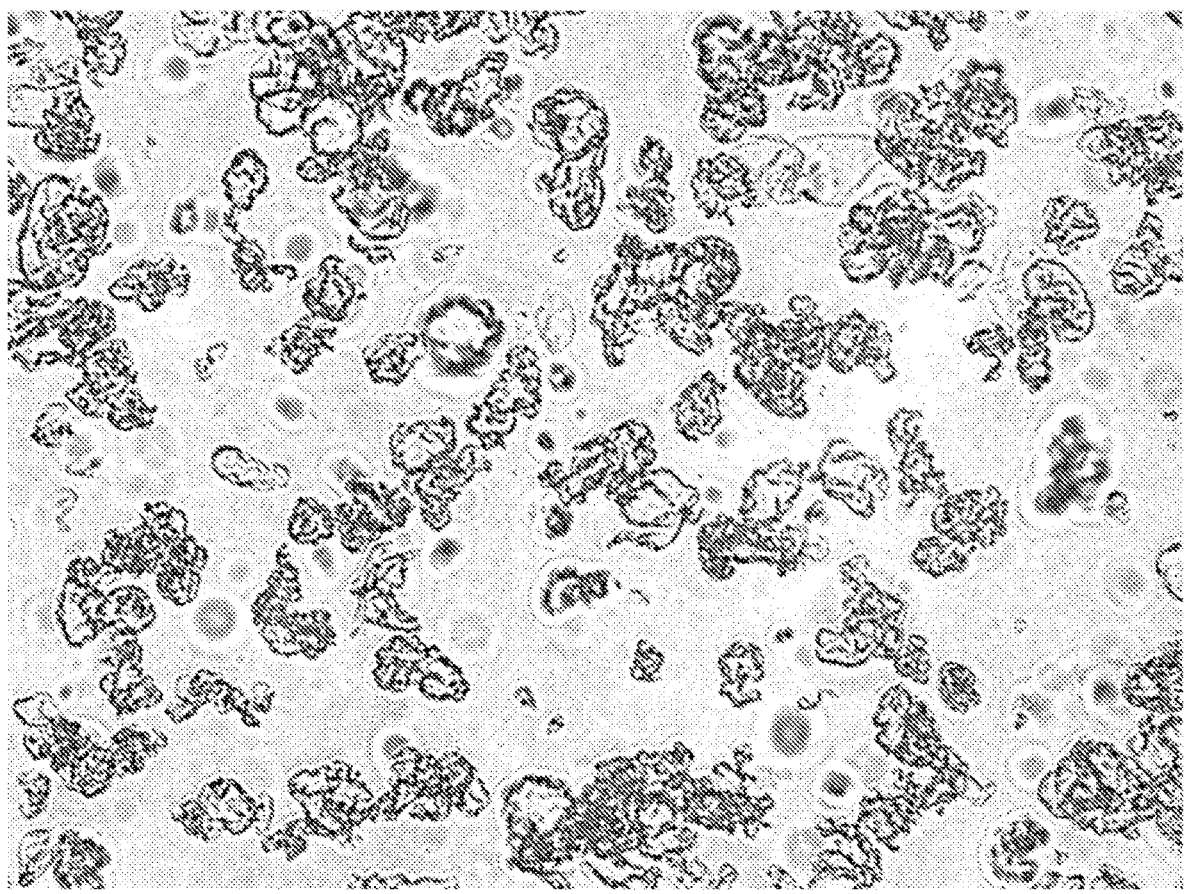
FIG. 5 shows a microscopy image of a liposomal suspension formed from RgnA10.
Figure 6:
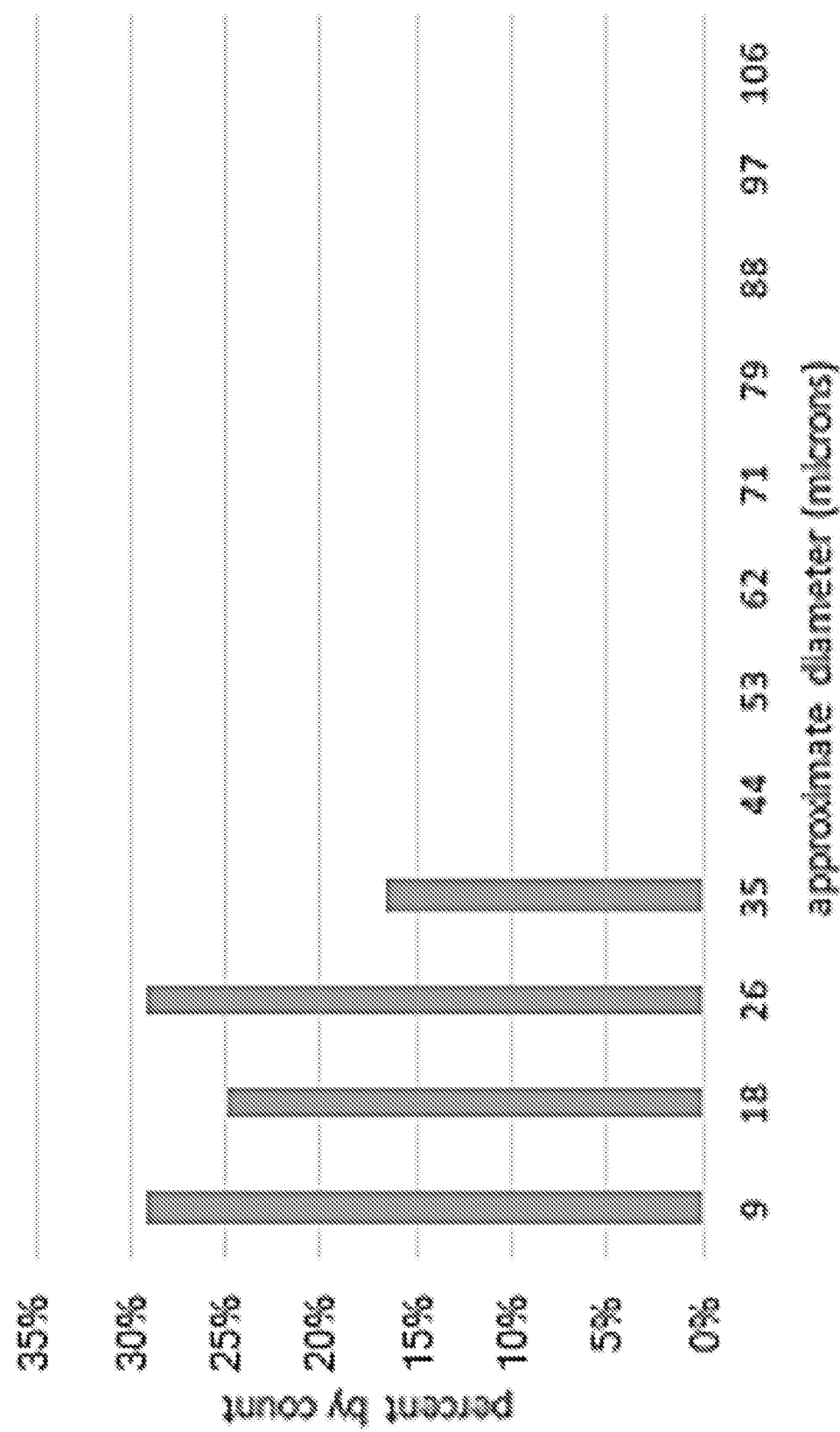
FIG. 6 shows a histogram of the approximate diameter of liposomes formed from RgnA10.

The pre-liposomal lyophilate appears as a white fluffy powder in a sterile vacuum vial. The process for rehydrating involves injecting a solution of concentrated adenosine into the vial. The powder then dissolves within 30 seconds, sometimes instantaneously, and may require gently swirling. The resulting liposomal suspension can then be removed from the vial via a syringe. Note that since the content of the vial is under vacuum, the adenosine solution will be quickly taken up by the vial upon insertion of the syringe. The ideal concentration of adenosine solution to use for rehydration is its maximum solubility in water, 7 mg/mL. For the diluent, sterile water for injection (SWFI) was used, but saline and buffered solutions can be used as well. A microscopic view of the resulting liposome suspension is shown in FIG. 5.

The average diameter of each particle is approximately 50 micrometers. In this example, we rehydrated 80 mg of powder in 11 ml of 7 mg/ml adenosine solution (in SWFI). Note that the microscopy image above is a dilution to be able to allow the viewing of separate liposomal particles.

Figure 10:
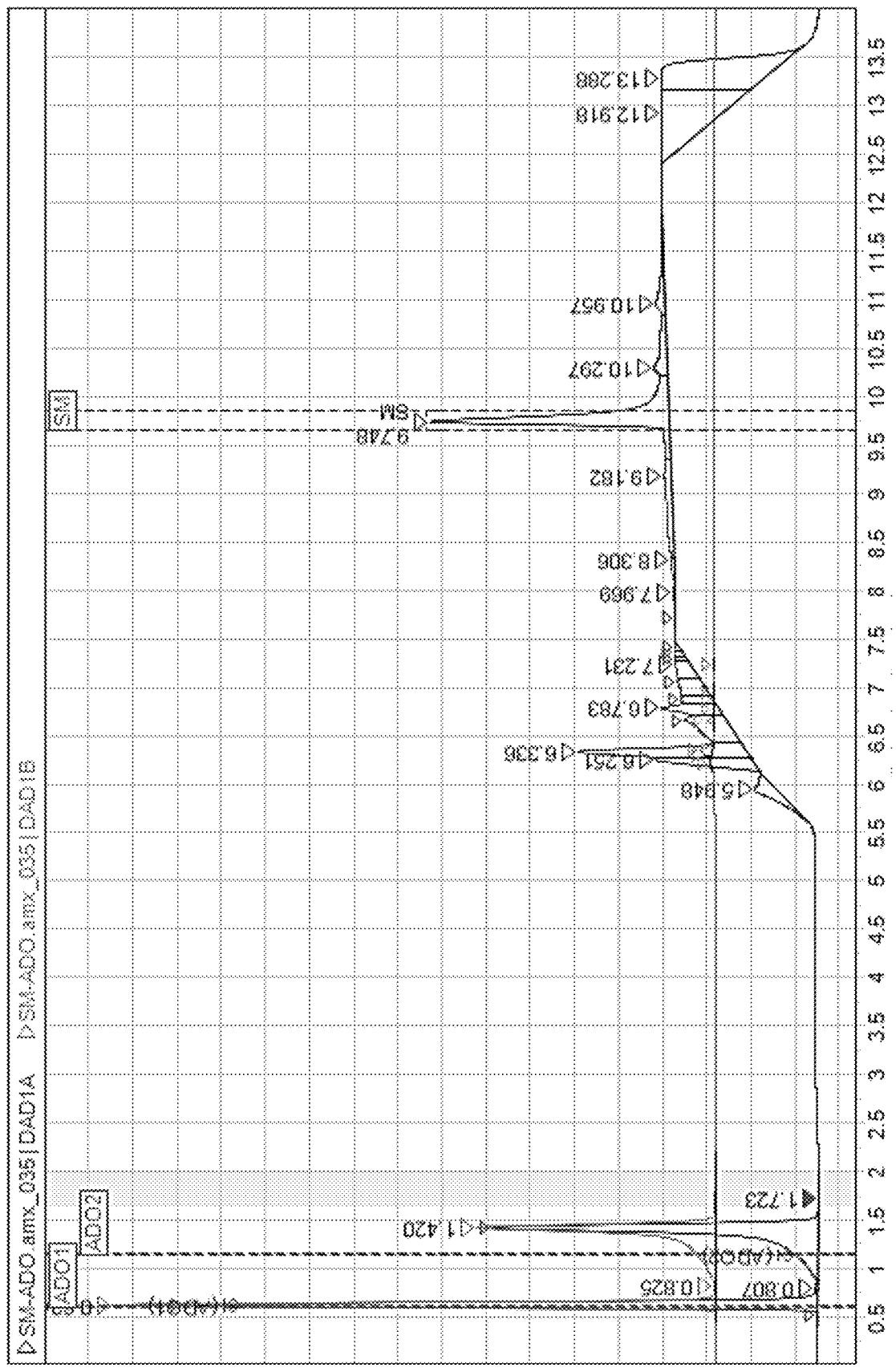
FIG. 10 shows an HPLC chromatogram of material isolated in Example 1.

An HPLC method for measuring both adenosine and lipid content was prototyped. The liposome formulation was subjected to centrifugation, and the pellet was separated from the supernatant. Complete dissolution of the pellet was obtained with methanol. The lipid portion of the liposome was relatively insoluble in acetonitrile, whereas adenosine is soluble in acetonitrile. Therefore, the HPLC method involved an initial mobile water/acetonitrile phase that first eluted adenosine from the HPLC column (which was a $C_{18}$ column), followed by a methanol mobile phase to elute the lipid. One standard for each agent was run: adenosine and lipid. The dissolved pellet was run and compared the result to those standards. The pellet chromatogram is shown in FIG. 10.

Figure 11:
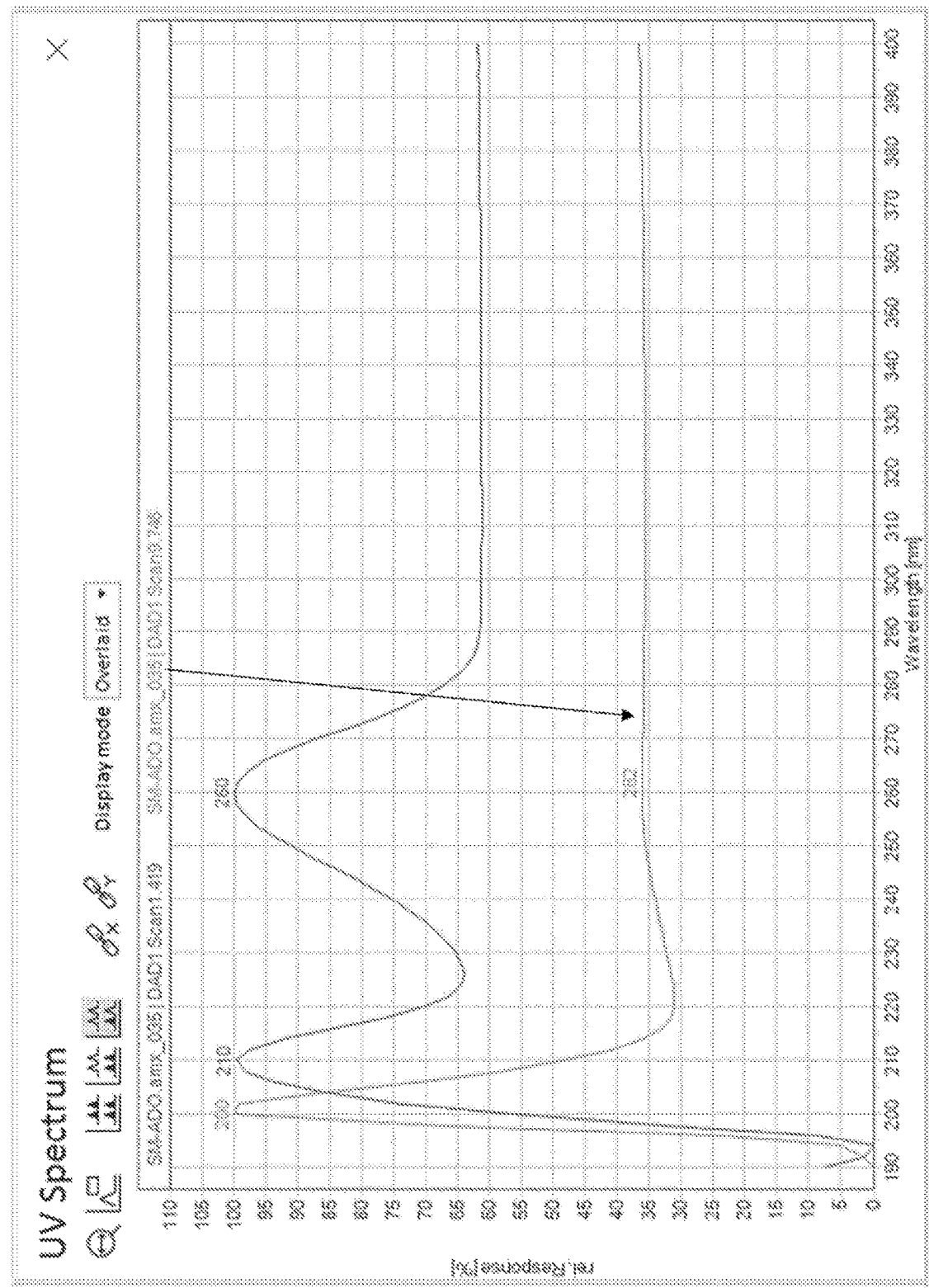
FIG. 11 shows the UV spectrum of the material isolated in FIG. 10.

The retention time of adenosine in this method is 1.42 minutes, and the retention time of the lipid is 9.75 minutes. The two analytes are also detected at different wavelengths: 260 nm and 203 nm for adenosine and lipid respectively. The FIG. 11 shows these spectra.

The lipid [SM] standard was 4 mg/mL and the adenosine [ADO] standard was 1 mg/ml. The resulting peak areas for the standard runs were as follows.

| SM | ADO |
|---|---|
| 22,521 | 25,783 |
| 22,317 | 25,072 |
| 22,558 | 25,158 |
| 22,465 | 25,338 |

In lieu of a calibration curve, the following was considered:

[SM]=SM122,465/4=SM/5,616
[ADO]=ADO/25,338

The pellet was then run in triplicate, and the following results were obtained for the two peaks.

| INDEX | ADO | SM |
|---|---|---|
| 1 | 8046 | 7157 |
| 2 | 8320 | 8387 |
| 3 | 8318 | 9764 |

The fraction of adenosine in the pellet (defined as [ADO]/([ADO]+[SM])) as a function of the ratio of chromatogram peak areas (ADO/SM) can be derived as follows:

$$[ADO] = ADO/25,338$$

$$[SM] = SM/5616$$

$$\frac{[ADO]}{[SM]} = \frac{ADO}{SM} 0.2216$$

$$\frac{[ADO]}{[ADO]+[SM]} = \frac{[ADO]/[SM]}{[ADO]/[SM]+[SM]/[SM]} = \frac{[ADO]/[SM]}{[ADO]/[SM]+1}$$

$$\frac{[ADO]}{[ADO]+[SM]} = \frac{\frac{ADO}{SM} \cdot 0.2216}{\left(\frac{ADO}{SM} 0.2216\right)+1}$$

When applied to the chromatogram results, the following values were obtained:

| INDEX | ADO | SM | ADO/SM | [ADO]/([ADO]+[SM]) |
|---|---|---|---|---|
| 1 | 8046 | 7157 | 1.124214056 | 19.94% |
| 2 | 8320 | 8387 | 0.992011446 | 18.02% |
| 3 | 8318 | 9764 | 0.851904957 | 15.88% |
|   |      |      |             | 17.95% |

Example 3

This example provides a description of methods of use of injectable formulations of the present disclosure.

Rats with established OA received an intra-articular injection of saline (100 μL) and other 8 groups of animals received Ade in 2 different liposomal formulations at the doses of, 3, 1, 0.3 and 0 mg/mL. The first injection was performed 4 weeks after the ACL rupture. Animals received one injection every 10 days, 6 times. Knee swelling was measured before every injection as a measure of articular inflammation. Pain test was performed in rats at baseline (before the first injection), 5 days after the $3^{rd}$ injection and finally at 57 days, right before sacrifice (7 days after the last injection). Post-sacrifice joints was analyzed using histology and uCT.

10 Treatment Groups
2 formulations×4 doses=8 treatment groups
1 positive control (Rgn01)
1 negative control (saline)

RgnA01 was prepared as described in Corciulo et al., Endogenous adenosine maintains cartilage homeostasis and exogenous adenosine inhibits osteoarthritis progression, Nat Commun. 2017 May 11; 8:15019.

Liposomes were prepared fresh the day before injection. Ethanol was added to soybean oil containing adenosine, or adenosine plus adenosine receptor antagonists. The lipid phase containing phosphatidyl choline and cholesterol (1:0.5 by molar ratio) was added to the previous solution and emulsified at 15,000 r.p.m. for 10 min. Saline along with glycerin was then added to the lipid phase and was homogenized at 15,000 r.p.m. for 20 min followed by sonication for 1 min at 100% duty cycle.

PTOA rats were randomized to experimental groups. Pain tests were performed before the beginning of the experiment (4 weeks after the ACL rupture) and 5 days after the 3d injection. Pain behavior was measured as weight bearing asymmetry between the ipsilateral and contralateral hind limbs using an incapacitance meter. After the hyperalgesia test animals were placed in a rodent restrainers to let them stand on their hind paws. Hind limbs were resting on the two weight averaging platform pads. As the animal shifts their weight from each pad, the unit recorded the average weight in grams over 12 seconds for 3-4 consecutive measurements. The mean value for each animals was used for the statistical analysis.

Example 4

This example provides a description of methods to prepare liposomes of the present disclosure and release kinetics of liposomes of the present disclosure.

Preparation of Pre-Liposomal Lyophilate:

| | Conditions | |
|---|---|---|
| Formulations | RgnA09 | RgnA10 |
| mg lipid | 100 | 100 |
| % SM | 75% | 100% |
| % PC/PG Mixture | 25% | 0% |
| % DMPC | 17.5% | 0.0% |
| % DMPG | 7.5% | 0.0% |
| SM (mg) | 75.00 | 100.00 |
| DMPC (mg) | 17.50 | 0.00 |
| DMPG (mg) | 7.50 | 0.00 |
| Hydrated with 3 mg/ml ADO Soln (ml) | 10 | 10 |
| Lipid in solution (mg/ml) | 10 | 10 |
| Dissolution time & diluent volume | Dissolved in less than 5 min. | Dissolved in less than 5 min. |

All vials contained 100 mg total and the fill volume was 5 mL, with a fill concentration 20 mg/ml solvent.

For RgnA09, 75 mg SM, 17.5 mg DMPC, and 7.5 mg DMPG was dissolved in 5 mL of a 1:1 (ratio by volume) of a water to tertiary-butyl alcohol (TBA) mixture. This solution was lyophilized with the following parameters (first freezing at −40° C. for 30 min, then primary drying at 10° C. for 20 h under a vacuum of 200 micron, followed by secondary drying at 20° C. for 4.5 h), and maintained in a vacuum-sealed vial. The lyophilate was then rehydrated with 40 mg of pure water at room temperature (25° C.).

For RgnA10, 100 mg of pure sphingomyelin (SM) was dissolved in 5 mL of a 3:2 (ratio by volume) of a water to tertiary-butyl alcohol (TBA) mixture. This solution was lyophilized with the following parameters (first freezing at −40° C. for 30 min, then primary drying at 10° C. for 20 h under a vacuum of 200 micron, followed by secondary drying at 20° C. for 4.5 h), and maintained in a vacuum-sealed vial. The lyophilate was then rehydrated with 40 mg of pure water at room temperature (25° C.)

Preparation of Adenosine stock solution: Adenosine stock solution was prepared by dissolving pure adenosine powder into saline buffer (0.9% saline). 50 mL of 0.9% saline was transferred into a sterile centrifuge tube, then 150 mg of adenosine was weighed and transferred into the saline rendering a 3 mg/ml stock solution. The solution was mixed via intermittent vigorous vortexing over the course of at least 30 minutes. The solution was then filtered into a new 50 mL centrifuge tube with a 0.2 µm sterile syringe filter to remove large undissolved adenosine particles, yielding a solution containing monomeric dissolved adenosine. Solutions were prepared at room temperature and were stored refrigerated (2-8° C.) after use.

Preparation of liposomal-adenosine suspension. Liposome solutions were initially prepared by the following procedure, starting with glass vials containing 100 mg of lyophilized lipid powder of the appropriate composition. Each vial of lipid was then hydrated by injecting 10 mL of adenosine stock solution (3 mg/ml in saline) into the vial and vigorously vortexing. Dissolving 100 mg of lipid in 10 mL of buffer was expected to yield solutions with 10 mg/mL total lipid. The liposomes formed are expected to be multilamellar with sizes ranging from 1-10 µm, with some larger and smaller liposomes possible.

24 h In-Vitro Release by Dialysis: Preparing the dialysis cassette: dialysis cassettes were primed for use following manufacturer's recommended protocol. Briefly, the dialysis cassette was filled with 5 mL of 20% EtOH (200 proof ethanol mixed with DI water as a 1:4 v/v ratio) and allowed to float in a glass beaker containing 500 mL of 20% EtOH for 10 minutes. No stir bar or stirring was used for this step. The dialysis cassette was then emptied by pipette and filled with 5 L DI water, and the 500 mL volume was discarded and replaced with 500 mL of DI water, and the dialysis cassette was allowed to float in the DI water for another 20 minutes (no spinning). The cassette was then considered suitable for use after removing the 5 mL DI water.

Preparing the dialysis chamber: 1 L glass beakers were filled with 500 mL of 0.9% saline as the external buffer. A magnetic stir bar was added to each glass beaker.

Dialysis cassettes were filled with 3 mL of the appropriate test solution, either 1) pure adenosine stock solution, or 2) multilamellar liposome+Ade solution.

Filled dialysis cassettes were then placed in the foam float ring and allowed to float in the 500 mL of 0.9% saline, with one dialysis cassette per 500 mL container. The stir plate was adjusted to maintain even stirring, without splashing and without funnel/vortex formation that might affect the cassette, at a rotation rate of 250-300 rpm. The zero-time point was taken as the time at which the sampled-filled cassette was first placed into beaker and stirring initiated.

Samples of the retentate (the solution inside of the dialysis cassette) were taken at various timepoints by first mixing the solution inside the cassette by gentle pipetting with a 1 mL pipette, then removing 50 µL and transferring it to a pre-labelled 1.5 mL Eppendorf tube.

Analysis of adenosine concentration was performed using a NanoDrop OneC spectrophotometer to measure the UV/Vis absorbance at 260 nm (baseline correction ON at 750 nm, automated pathlength off). The measurements were all blanked against 0.9% saline. UV/Vis measurements were made using 2 µL samples pipetted onto the instrument pedestal, with a total n=3 measurements (three×2 µL volumes, cleaning the pedestal between each measurement by wiping with a lint-free wipe) per sample condition time point.

10 day In-vitro release kinetics: Liposomal lyophilates in sterile glass vials were mixed with sterile adenosine solution (3 mg/ml, in saline) provided in pre-filled plastic syringes (custom order from Mycoscience Inc). Samples of the Lipo-adenosine suspension (100 µl) were incubated in phosphate-buffered saline for 0, 1, or 2 h, and 1, 2, 5, 7, or 10 days at 37° C. At the end of each incubation time, samples were centrifuged at 23,000×g for 15 min at 4° C. Supernatant was removed, and the liposome pellet re-suspended in a saline solution containing 0.5% Triton-X100. Adenosine concentration in the remaining intact liposomes was quantified by high-performance liquid chromatography (HPLC).

Animal study: Rats with established OA received intraarticular injection of saline (100 ul) and other 8 groups of animals will receive Ade in 2 different formulations at the doses of 3, 1, 0.33 and 0 mg/ml. The first injection was performed 4 weeks after the ACL rupture. Animals received one injection every 10 days, 6 times. Knee swelling was measured before every injection as a measure of articular inflammation. Pain tests were performed in rats at baseline (before the first injection), after 30 days before the 3rd injection and finally at 57 days, right before sacrifice (7 days after the last injection). A test of pain and a motor test were performed, the incapacitance test (measured as weight bearing asymmetry between the ipsilateral and contralateral hind limbs by incapacitance meter) and the rotarod test (time that the rat was able to continue running on a rotating rod before falling off). Post-sacrifice joints will be analyzed using histology and uCT.

Figure 13:
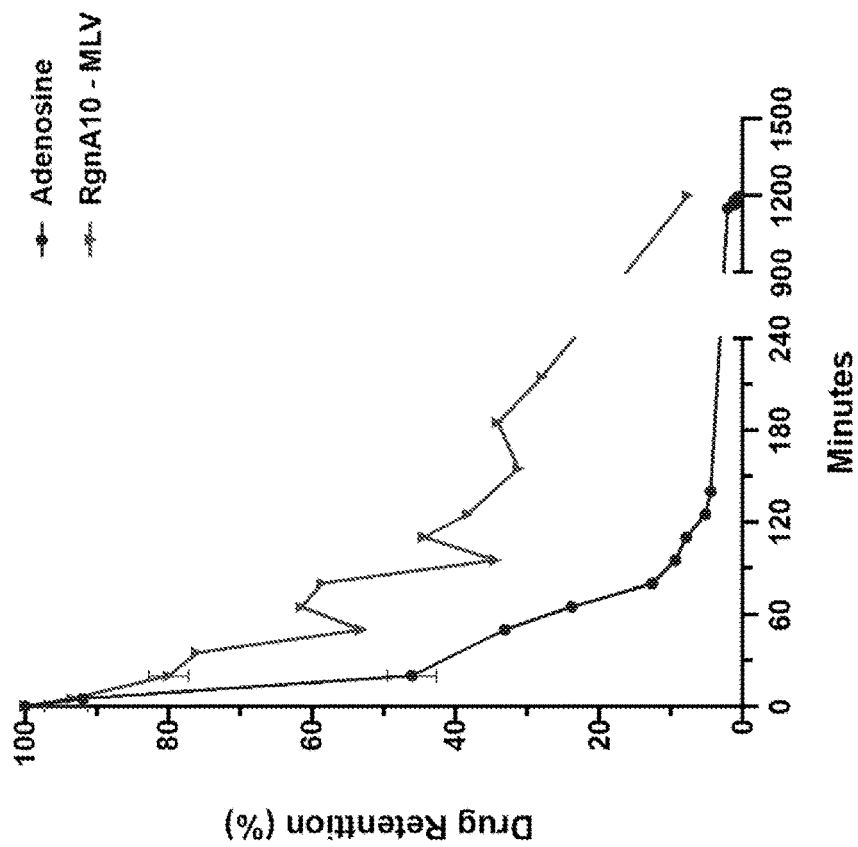
FIG. 13 shows the release kinetics of adenosine over 24 hours from (left) RgnA09-MLV and (right) RgnA10-MLV.
Figure 13:
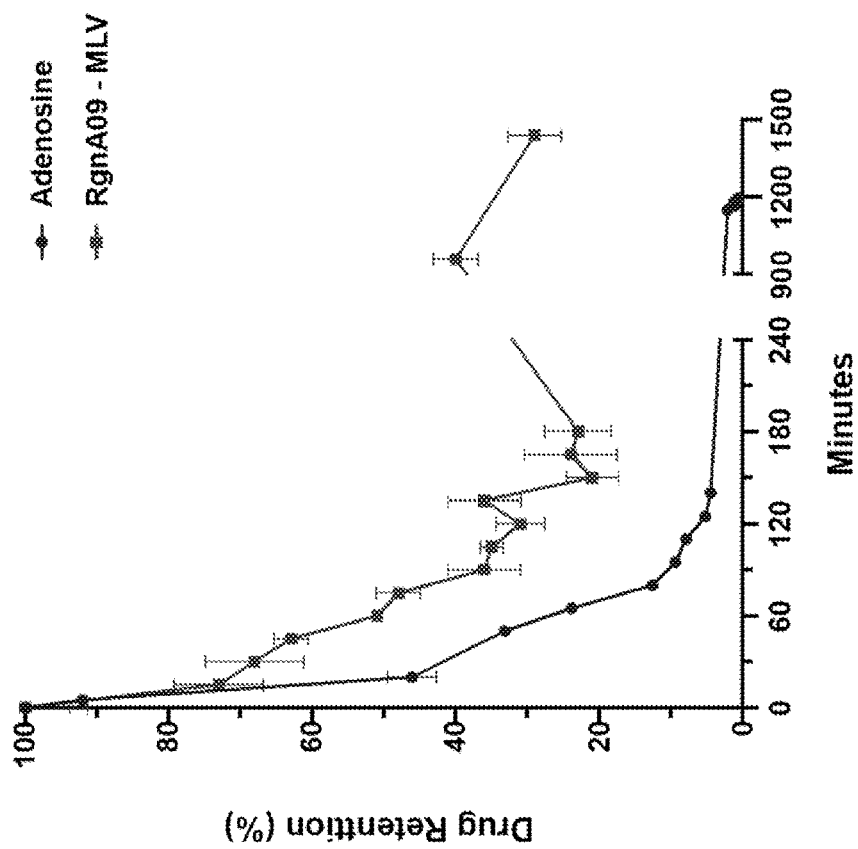

24 h In-Vitro Release by Dialysis: FIG. 13 shows that the non-liposomal adenosine is released over time. However, RgnA09 effectuates an overall 21.86% to 37.90% higher dose due to a slow release of the liposomal-adenosine due to a higher retention of the drug in liposomes and several bursts of release around 2 hrs and 16 hrs, resulting in 25.76% and 37.90% higher dose. In contrast, RgnA10 effectuates an overall 26.61% to 49.27% higher dose due to a slow release of the liposomal-adenosine due to a higher retention of the drug in liposomes and several bursts of release around 1 hr, 2 hrs and 3 hrs, resulting in 48.89%, 39.21% and 29.65% higher dose.

Figure 12:
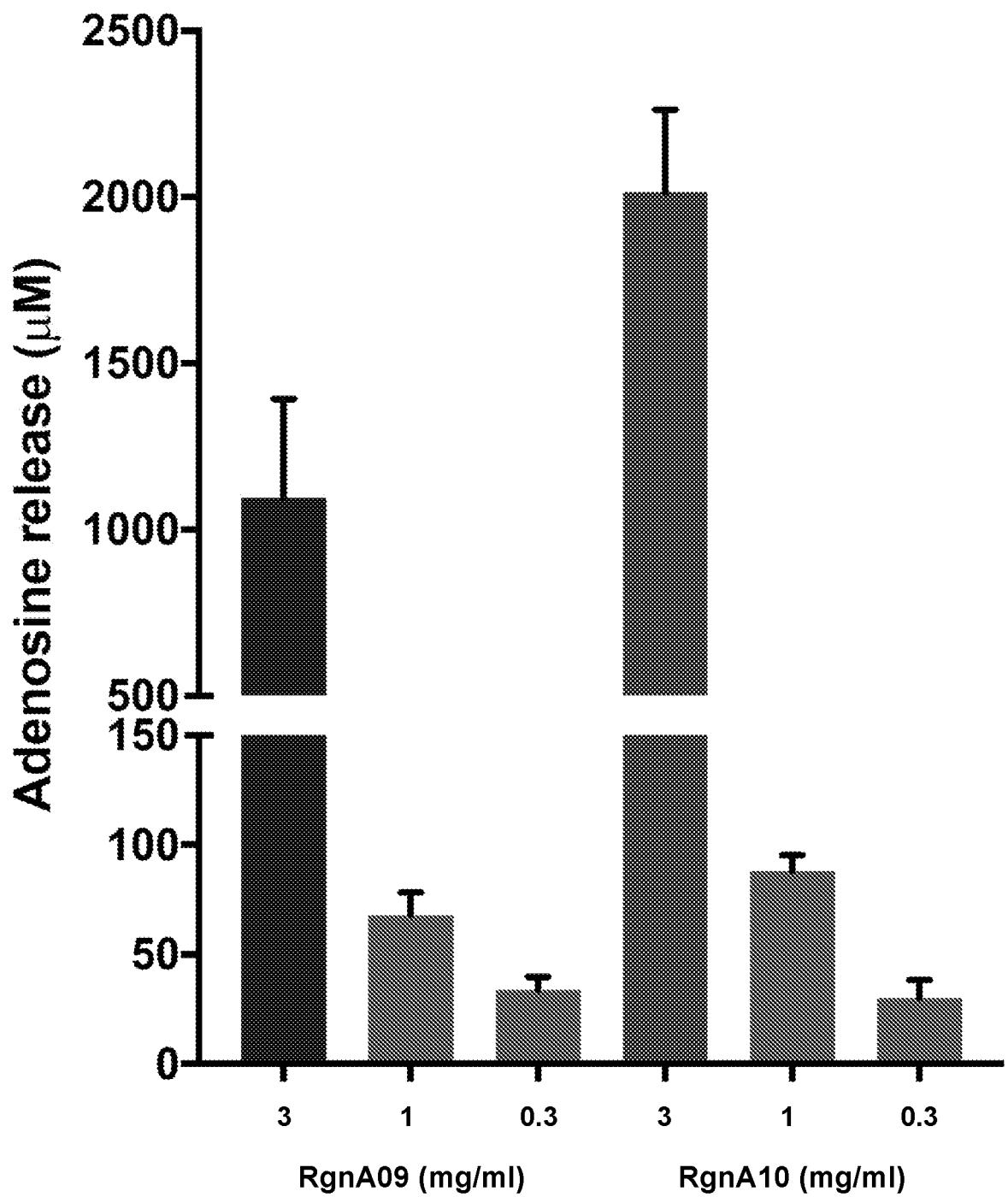
FIG. 12 shows the initial bolus release of RgnA09 and RgnA10.

10 day In-vitro release kinetics: FIG. 12 shows the percent adenosine retention in both liposomal formulations. There is an initial bolus release of adenosine (1096 µM with RgnA09; 2014 µM with RgnA10). No significant difference has been detected between RgnA09 and RgnA10 formulations. Fresh prepared liposome suspension (time 0) shows 21% retention of adenosine for RgnA09 and 19% for RgnA10. FIG. 1 and FIG. 4 show after 1 h of incubation, retention drops to 4% for both formulations, slowly decreasing over time to reach 1.4% and 2% (RgnA09 and RgnA10, respectively) at day 10, corresponding at 159 μM and 227 μM adenosine. These results show that both liposomal formulations are good reservoirs for encapsulation and slow release of adenosine in concentrations sufficient to activate A2A receptor in vivo.

Animal study: We further tested the efficacy of the newly developed formulations in the post-traumatic OA (PTOA) rat model. As described above, rats develop OA after mechanical rupture of the ACL. PTOA rats were randomized to experimental groups. Incapacitance pain tests were performed prior to beginning the experiment. Animals were divided into 10 groups, to receive RgnA09 or RgnA10 at 0 (empty liposome/vehicle), 0.3, 1, or 3 mg/ml of adenosine, saline, or formulation, as described previously in Corciulo et al. Animals received one injection every 10 days, 6 times. Knee swelling was measured before every injection as a measure of articular inflammation. Pain test was performed in rats at baseline (before first injection), at 30 days (mid-term of the treatment regimen), and right before sacrifice (7 days after the last injection). Post-sacrifice joints were analyzed using histology and uCT. Pain behavior was measured as weight bearing asymmetry between the ipsilateral and contralateral hind limbs by incapacitance meter and by the rotarod test.

Figure 9:
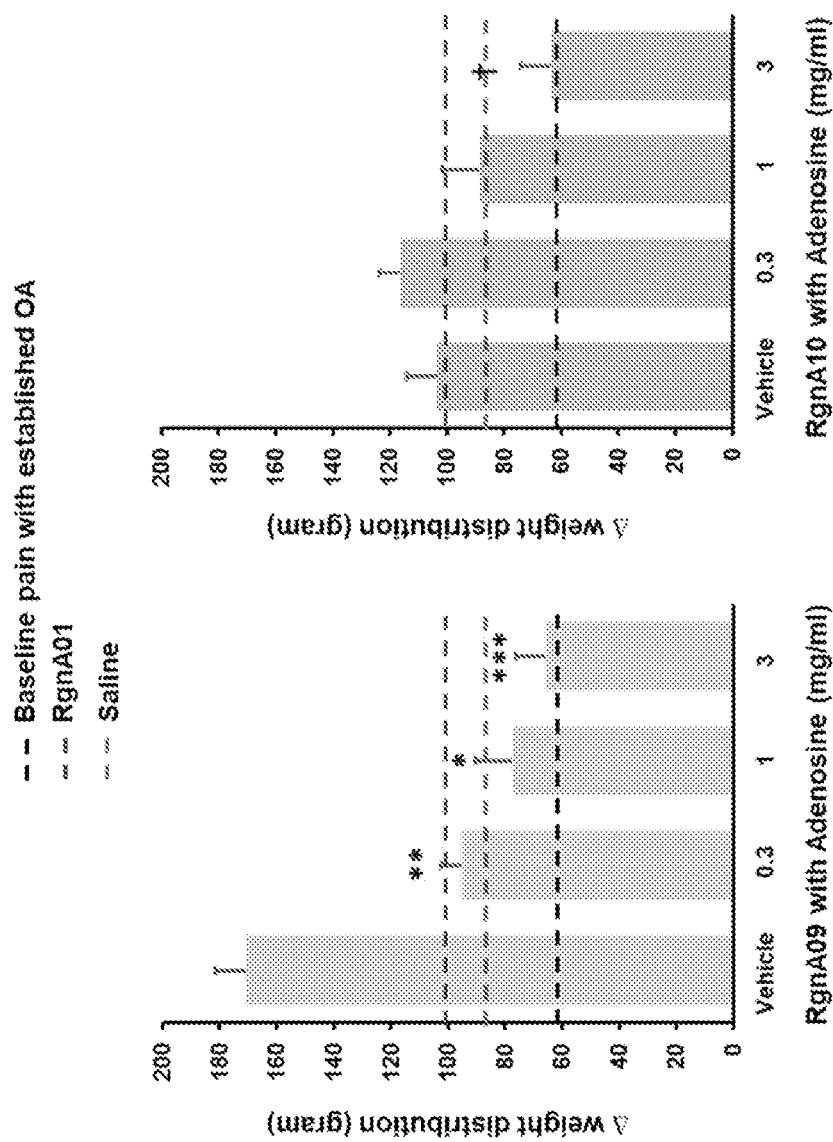
FIG. 9 shows recorded pain data using an incapacitance test.
Figure 14:
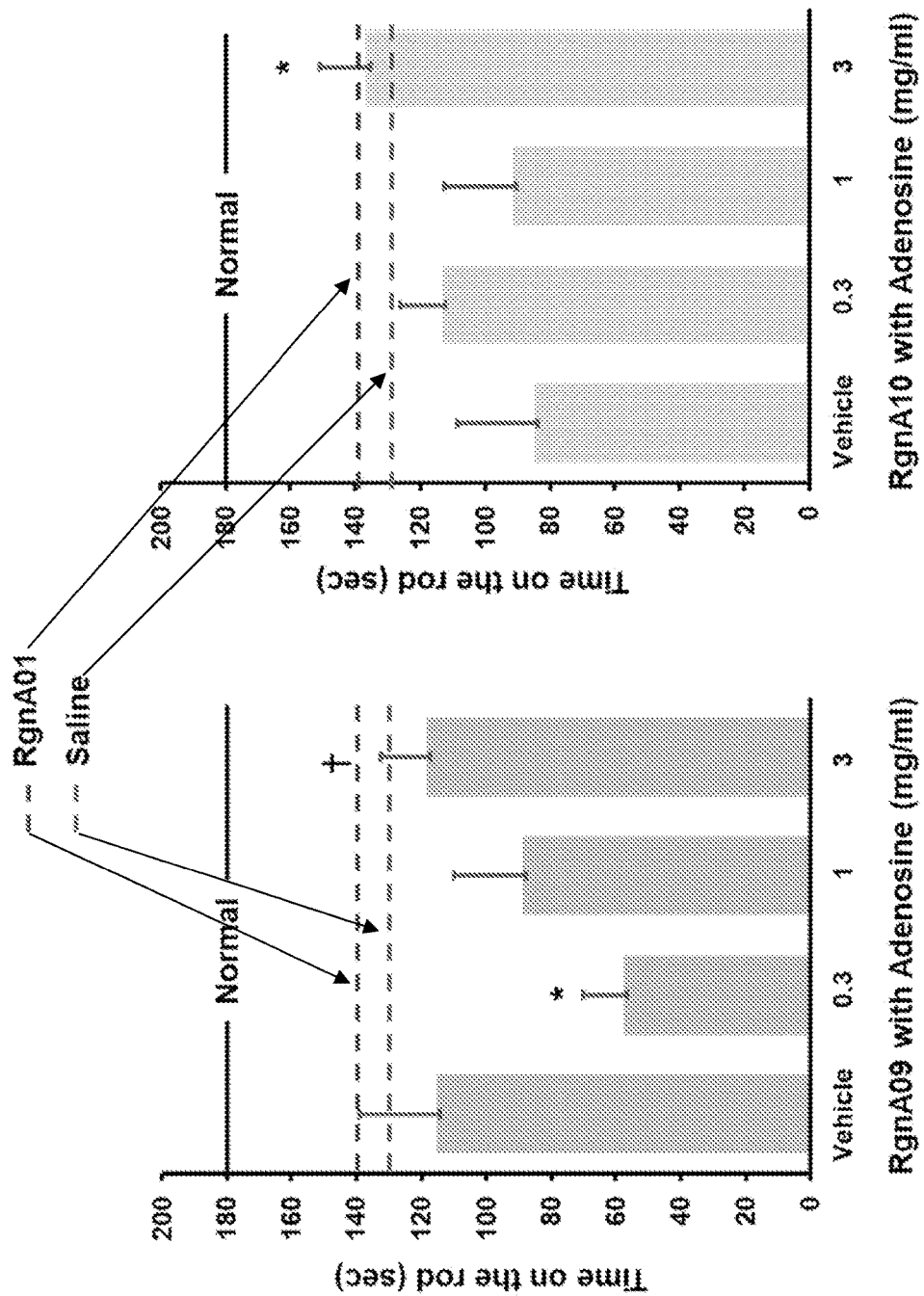
FIG. 14 shows rotarod pain test at 60 days (after six injections) with (left) RgnA09 and (right) RgnA10.
Figure 15:
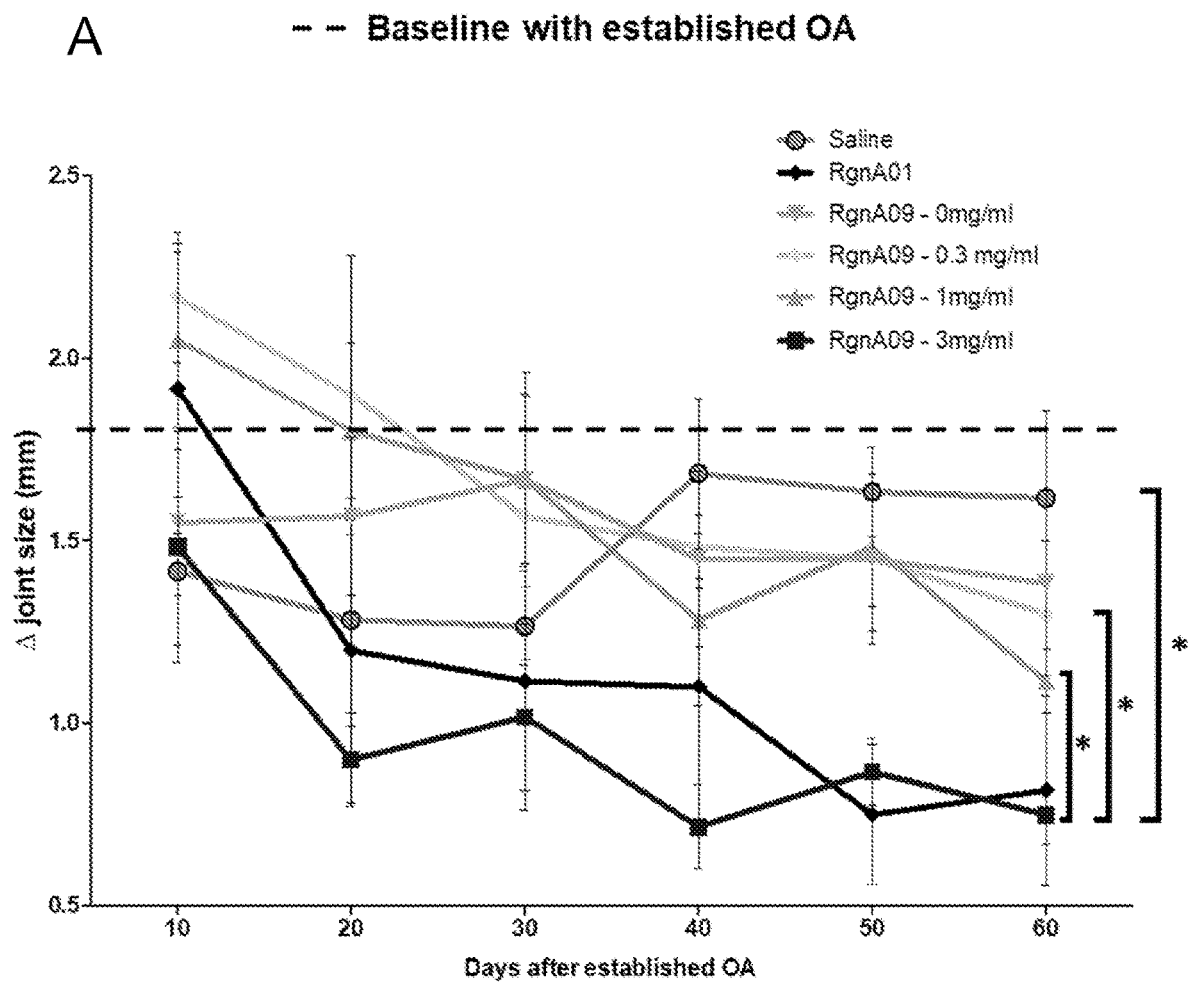
FIG. 15 shows the effect of (A) RgnA09 and (B) RgnA10 on joint inflammation at various concentrations over 6 injections. Administration was ipsilateral-contralateral. Statistics: One-way (Brown-Forsythe and Welch) ANOVA. *$P<0.05$ v/s vehicle, †$P<0.05$ v/s saline, +$P<0.05$ v/s 0.3 mg and 1 mg.
Figure 15:
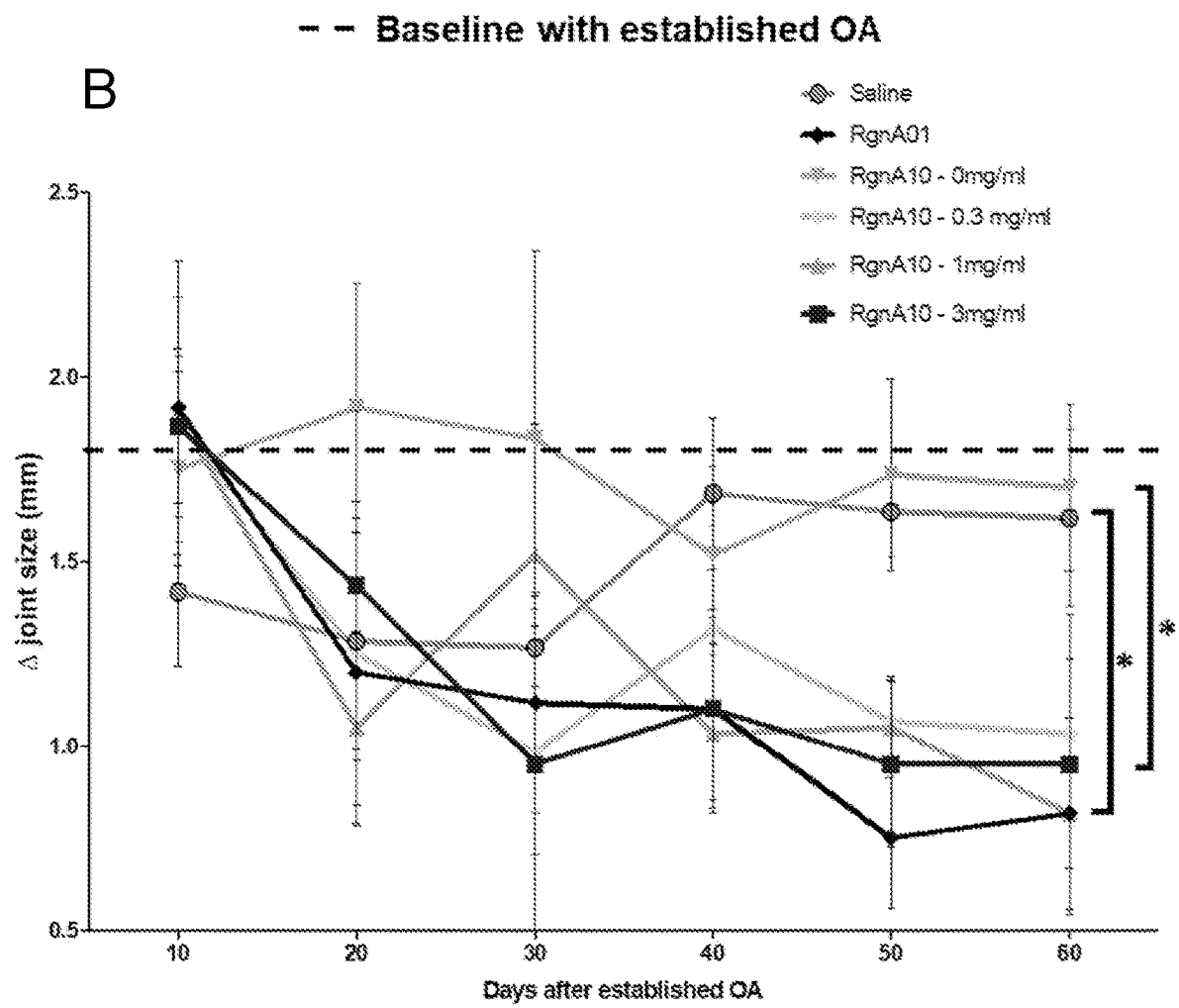

Animals were placed in rodent restrainers to stand on hind paws, with hind limbs resting on two weight-averaging platform pads. As the animal shifted their weight from each pad, the unit recorded the average weight in grams over 12 seconds for 3-4 consecutive measurements. The mean value for each animal was used for analysis. Pain was also measured using the rotarod test, which provides assessment of motor function with pressure and stress on the knee joint. Rats were placed onto an accelerating rotarod, and failure to stay atop the rod was measured and used for further analysis Based on the incapacitance test, there was a strong reduction in pain behavior between animals treated with intra-articular vehicle and 1 mg/ml for RgnA09, and between 0.3 mg and 3 mg with RgnA10. In addition, at 30 days (after 3 injections) we observed a steady trend of a dose response in the reduction of joint pain with both formulations, with all doses significantly different from vehicle for Rgn09, and 3 mg of Rgn10 different from Rgn01 and vehicle (FIG. 9). The rotarod test also showed a dose-response trend and a difference at 60 days with the highest dose of Rgn10 (3 mg/ml) (FIG. 14). In addition, we observed remarkable changes in joint inflammation with both formulations, with some doses showing significant differences to vehicle and saline after 6 injections. There was a steady decrease in joint inflammation over time with both formulations at 3 mg/ml (FIG. 15). Both Rgn09 and Rgn10 were used at the highest dose of 3 mg/ml.

Figure 16:
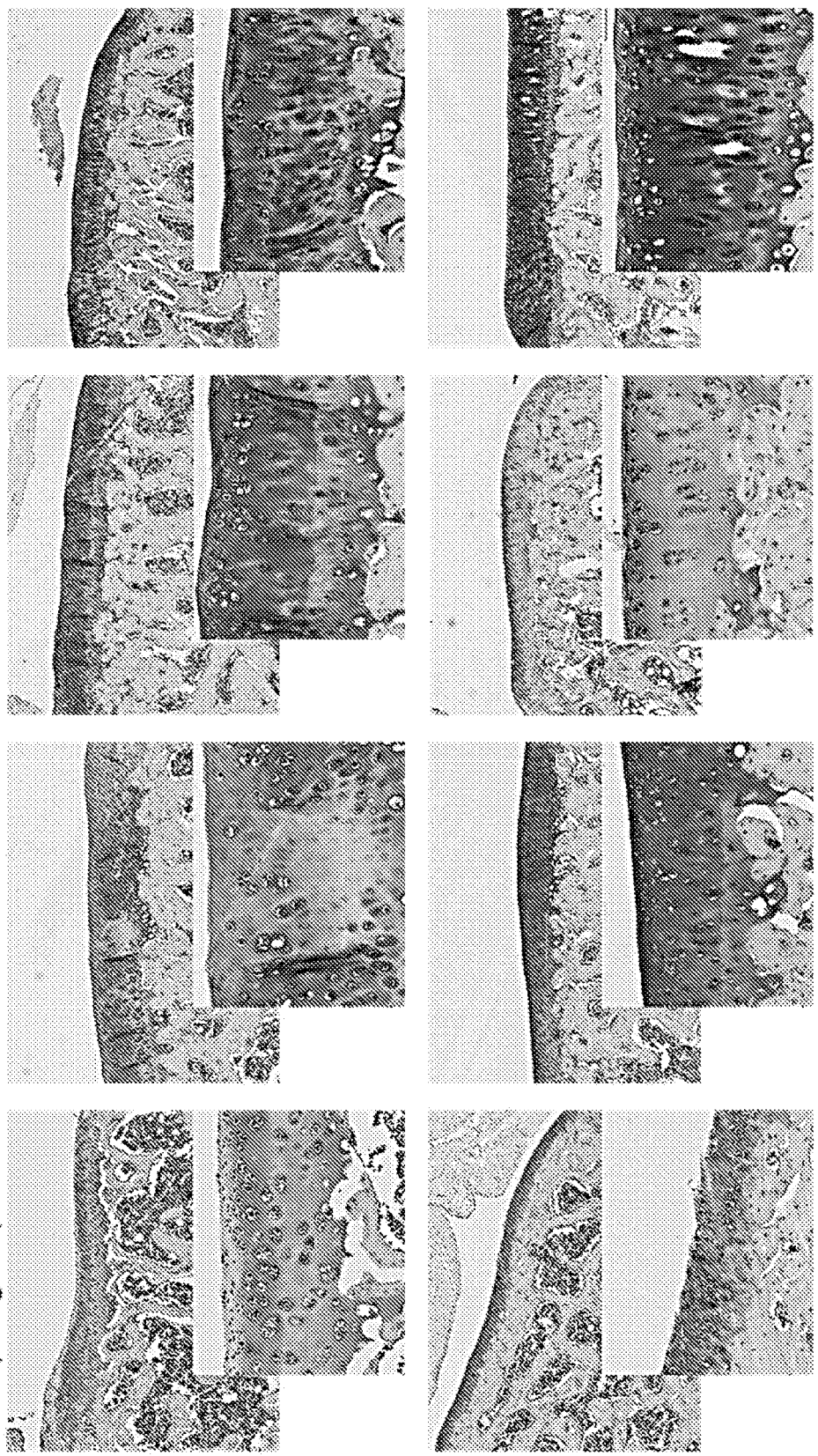
FIG. 16 shows representative safranin O-stained sections of the affected rat tibias after treatment with vehicle or 3 doses of liposomal adenosine. In the vehicle-treated animals there was a marked reduction in cartilage proteoglycan and surface irregularity of the cartilage. There was a dose-dependent improvement in cartilage proteoglycan and loss of fraying of the cartilage in the RgnA09-treated rats with increased surface cartilage. In the RgnA10-treated rats the effect was strongest in the cartilage of those treated with the highest dose studied (3 mg/ml) although preservation of the cartilage was observed at the lower doses as well.

Shown in FIG. 16 are representative safranin O-stained sections of the affected rat tibias after treatment with vehicle or 3 doses of liposomal adenosine. In the vehicle-treated animals there was a marked reduction in cartilage proteoglycan and surface irregularity of the cartilage. There was a dose-dependent improvement in cartilage proteoglycan and loss of fraying of the cartilage in the RgnA09-treated rats with increased surface cartilage. In the RgnA10-treated rats the effect was strongest in the cartilage of those treated with the highest dose studied (3 mg/ml) although preservation of the cartilage was observed at the lower doses as well.

Conclusion: The new formulations of liposomal adenosine were as effective, if not more effective, at relief of both pain and swelling in the OA knees with concomitant preservation and enhancement of cartilage. Both formulations were effective and the in vitro release of adenosine from the multilamellar vesicles was superior to the non-liposomal or free adenosine.

Example 5

This example provides a methods of using liposomes of the present disclosure.

Shelf-stable formulations RgnA09 and RgnA10. Developed and evaluated was a series of shelf-stable formulation options based on lipid constituents, solubility efficiency, and retention properties. RgnA09 and RgnA10 can be rehydrated in a concentrated solution of a hydrophilic adenosine. In the process of said rehydration, multi-lamellar liposomal particles are created that contain adenosine in the liposome's aqueous compartment. The liposomes are ~10-100 microns in size and are meta-stable, such that they collapse into a dense form in a hyperthermic environment (~40° C.). The liposomes effectuate sustained release of adenosine when constrained to a local closed compartment, such as within the bursa of the synovial joint of a human knee. RgnA09 and RgnA10 were tested in order to assess their ability to incorporate and release adenosine over time. Liposomal lyophilates in sterile glass vials were mixed with sterile adenosine solution (3 mg/mL, in saline) provided in pre-filled plastic syringes (custom order from Mycoscience Inc). Samples of the Lipo-adenosine suspension (100 μL) were incubated in phosphate-buffered saline for 0, 1, or 2 h, and 1, 2, 5, 7, or 10 days at 37° C. At the end of each incubation time, samples were centrifuged at 23,000×g for 15 min at 4° C. Supernatant was removed, and the liposome pellet re-suspended in a saline solution containing 0.5% Triton-X100. Adenosine concentration in the remaining intact liposomes was quantified by high-performance liquid chromatography (HPLC). FIGS. 1, 4, and 12 shows the percent adenosine retention in both liposomal formulations. There is an initial bolus release of adenosine (1096 μM with RgnA09; 2014 μM with RgnA10). No significant difference has been detected between RgnA09 and RgnA10 formulations. Fresh prepared liposome suspension (time 0) shows 21% retention of adenosine for RgnA09 and 19% for RgnA10. After 1 h of incubation, retention drops to 4% for both formulations, slowly decreasing over time to reach 1.4% and 2% (RgnA09 and RgnA10, respectively) at day 10, corresponding at 159 μM and 227 μM adenosine. These results show that both liposomal formulations are good reservoirs for encapsulation and slow release of adenosine in concentrations sufficient to activate A2A receptor in vivo.

The efficacy of the newly developed formulations was further tested in the post-traumatic OA (PTOA) rat model. As described above, rats develop OA after mechanical rupture of the ACL. PTOA rats were randomized to experimental groups. Incapacitance pain tests were performed prior to beginning the experiment. Animals were divided into 10 groups, to receive RgnA09 or RgnA10 at 0 (empty liposome/vehicle), 0.3, 1, or 3 mg/ml of adenosine, saline, or formulation, as described previously in Corciulo et al. Animals received one injection every 10 days, 6 times. Knee swelling was measured before every injection as a measure of articular inflammation. Pain test was performed in rats at baseline (before first injection), at 30 days (mid-term of the treatment regimen), and right before sacrifice (7 days after the last injection). Post-sacrifice joints were analyzed using histology and uCT. Pain behavior was measured as weight bearing asymmetry between the ipsilateral and contralateral hind limbs by incapacitance meter (FIG. 9).

After the hyperalgesia test, animals were placed in rodent restrainers to stand on hind paws, with hind limbs resting on two weight-averaging platform pads. As the animal shifted their weight from each pad, the unit recorded the average weight in grams over 12 seconds for 3-4 consecutive measurements. The mean value for each animal was used for analysis. Motor ability was also measured using the rotarod test, which provides assessment of motor function with pressure and stress on the knee joint. Rats were placed onto an accelerating rotarod, and failure to stay atop the rod was measured and used for further analysis (data not shown). Based on the incapacitance test, there was a strong dose interaction between vehicle and 1 mg/ml for RgnA09, and between 0.3 mg and 3 mg with RgnA10. In addition, at 30 days (after 3 injections) we observed a steady trend of a dose response in the reduction of joint pain with both formulations, with all doses significantly different from vehicle for Rgn09, and 3 mg of Rgn10 different from Rgn01 and vehicle. The rotarod test also showed a dose response trend and a difference at 60 days with the highest dose of Rgn10 (3 mg/ml). In addition, we observed remarkable changes in joint inflammation with both formulations, with some doses showing significant differences to vehicle and saline after 6 injections. There was a steady decrease in joint inflammation over time with both formulations at 3 mg/ml (FIG. 15). Both Rgn09 and Rgn10 may be used at the highest dose of 3 mg/ml.

Although the present disclosure has been described with respect to one or more particular examples, it will be understood that other examples of the present disclosure may be made without departing from the scope of the present disclosure.

The invention claimed is:

1. An injectable formulation comprising saline and liposomes comprising one or more lamellae, wherein the liposome lamellae comprise 70 to 100% by mass sphingomyelin and when there is less than 100% by mass sphingomyelin the remainder is 1,2-dimyristoyl-sn-glycero-3-phosphocholine (DMPC) or 1,2-dimyristoyl-sn-glycero-3-phosphorylglycerol (DMPG) or DMPC and DMPG together, wherein the liposomes
   (a) have a diameter of 50 nm to 150 µm; and
   (b) encapsulate adenosine in the aqueous compartment of the liposome, wherein the concentration of adenosine is 3 mg/mL.

2. The injectable formulation of claim 1, wherein the adenosine or a portion thereof is released for up to two weeks.

3. The injectable formulation of claim 1, further comprising an excipient.

4. The injectable formulation of claim 1, wherein the formulation is suitable for intra-articular injection.

5. The injectable formulation of claim 1, wherein the ratio of DMPC and DMPG is from 6:4 to 8:2.

6. The injectable formulation of claim 5, wherein the ratio of DMPC and DMPG is 7:3.

7. The injectable formulation of claim 1, wherein the total lipid concentration is 7 to 12 mg/mL.

8. The injectable formulation of claim 1, wherein one or more of the liposomes have a diameter of 50 nm to 100 µm.

9. The injectable formulation of claim 1, wherein one or more of the liposomes have a diameter of 100 nm to 150 µm.

10. The injectable formulation of claim 1, wherein the liposomes collapse at a temperature of 35 to 45° C.

11. The injectable formulation of claim 1, wherein at least a portion of the adenosine is released within 1 second to 1 hour of administration to a joint of an individual.

12. The injectable formulation of claim 11, wherein at least a portion of the adenosine is released within 1 minute to 1 hour of administration to the joint of the individual.

13. The injectable formulation of claim 12, wherein at least 1 to 20% of the adenosine is released within 1 minute to 1 hour of administration to the joint of the individual.

14. The injectable formulation of claim 11, wherein at least a portion of adenosine or at least 1 to 20% of adenosine is released within 1 second to 10 minutes of administration to the joint of the individual.

15. The injectable formulation of claim 1, wherein the liposomes have a diameter of 50 nm to 1 µm.

16. The injectable formulation of claim 1, wherein the liposomes have a diameter of 1 µm to 150 µm.

17. The injectable formulation of claim 1, wherein the liposome lamellae comprise 75 to 100% by mass sphingomyelin.

18. A method of i) inducing cartilage regeneration and/or ii) alleviating joint pain and/or inflammation and/or iii) slowing and/or arresting and/or reversing progressive structural tissue damage comprising administering to an individual an injectable formulation of claim 1, wherein i) cartilage regeneration is induced and/or ii) joint pain and/or inflammation is alleviated or partially alleviated and/or iii) progressive structural tissue damage is slowed or partially slowed and/or arrested or partially arrested and/or is reversed or partially reversed.

19. The method of claim 18, wherein the injectable formulation is administered via intra-articular injection to a joint of the individual.

20. The method of claim 18, wherein the injectable formulation is administered in one or more injections.

21. The method of claim 18, wherein the injectable formulation is administered multiple times, wherein each administration occurs once every 10 days.

22. The method of claim 18, wherein the individual has osteoarthritis, rheumatoid arthritis, acute gouty arthritis, and/or synovitis.

23. The method of claim 19, wherein the individual is a human or a non-human mammal.

* * * * *